(12) United States Patent
Zhu et al.

(10) Patent No.: US 7,414,125 B2
(45) Date of Patent: Aug. 19, 2008

(54) CLONING AND CHARACTERIZATION OF MICRORNAS FROM RICE

(75) Inventors: Jian-Kang Zhu, Riverside, CA (US); Ramanjulu Sunkar, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/393,206

(22) Filed: Mar. 29, 2006

(65) Prior Publication Data

US 2006/0236429 A1 Oct. 19, 2006

Related U.S. Application Data

(60) Provisional application No. 60/666,780, filed on Mar. 30, 2005.

(51) Int. Cl.
*C12N 15/00* (2006.01)
*C12N 15/09* (2006.01)
*C12N 15/11* (2006.01)
*C12N 15/82* (2006.01)
*C07H 21/02* (2006.01)

(52) U.S. Cl. ............... 536/24.5; 536/23.1; 435/468; 435/320.1; 800/285; 800/295

(58) Field of Classification Search ............ None
See application file for complete search history.

(56) References Cited

OTHER PUBLICATIONS

Vaucheret et al 2004 Genes and Development 18:1187-1197.*

\* cited by examiner

*Primary Examiner*—Russell Kallis
*Assistant Examiner*—Brent Page
(74) *Attorney, Agent, or Firm*—Townsend and Townsend and Crew LLP

(57) ABSTRACT

The present invention provides new miRNAs in rice. The nucleic acids of the invention can be used to control gene expression in plants.

4 Claims, 17 Drawing Sheets

A.

| | | |
|---|---|---|
| OsmiR396a,b | UUCCACAG-CUUUCUUGAACUG | (21 bp) |
| OsmiR396c | UUCCACAG-CUUUCUUGAACUU | (21 bp) |
| P33-D7 | UCCACAGGCUUUCUUGAACUG | (21 bp) |

B.

| | | |
|---|---|---|
| OsmiR399a | UGCCAAAGGAGAG-AAUUGCCCUG | (21 bp) |
| OsmiR399j,K | UGCCAAAGGAG-AGUUGCCCUA | (21 bp) |
| OsmiR399e | UGCCAAAGGAG-AUUUGCCCAG | (21 bp) |
| OsmiR399g | UGCCAAAGGAG-AUUUGCCCGG | (21 bp) |
| OsmiR399h | UGCCAAAGGAG-ACUUGCCCAG | (21 bp) |
| OsmiR399d,i | UGCCAAAGGAG-AGCUGCCCUG | (21 bp) |
| P7-A07 | UGCCAAUGGAGUAGUUGCCCUG | (22 bp) |

| | |
|---|---|
| Rice | UUGCUGCCUCAAGCUUGCUGC |
| wheat | UUGCUGCCUCAAGCUUGCUGC |
| Barley | UUGCUGCCUCAAGCUUGCUGC |
| Maize | UUGUUGCCUCAAGCUUGCUGC |
| Sorghum | UUGUUGCCUCAAGCUUGCUGC |
| Sugarcane | UUGUUGCCUCAAGCUUGCUGC |

B.

Rice

Wheat

Barley

Maize

Sorghum

Sugarcane

```
11667.m02576 5'    567 UCGAACAACCGCGGUUCGACA 588.....599 UCGAACAACCACAGUUCGACA 619 3'
                       ||||||||||||||||||||                ||||||||| | ||||||||
miRNA P28-E3       3'  AGCUUGUUGGGCGCCAAGCUGU  5'     3'  AGCUUGUUGGGCGCCAAGCUGU  5'
```

Predicted fold-back structures of the new miRNA precursors from rice.

```
OsmiR435 (ΔG= -121.6)

CU--       -- A   CG             A        C            CAU -  .-CCUAGCA       A UG        .-CC    A  A      AGUCGA
AACA
     ACUCUU CUU GUCUA  UUUCAUCUCUCAACUCCAA ACUGGA AAAACAUGUCCCU  CU UC         CUAGUUUAG G GUUUUUGC  AUGUGG CU CUUGGCU   CU UGCAU
A
     UGAGAA GAA CAGGU  AAAGUAGGGAGURGAGGUU UGGCCU UUUUGUACAGGGA  GA AG         GAUUAAGUU C UAAAAGCG  UGUACC GA GAAUCGA   GA AUGUA
A
UAUU      CU   C   UA           A        A            UUU U \ -------         C GU       \ --     - -       GUGG-- C
CAGU

OsmiR437 (ΔG= -100.0)

UG  UU    U      G       A    U            U    AAUUAACAUCUAAAAU     AU     CA- A
CCCUCUGUUUCAUAU  UA  GUGUUU AGUUUUGUU UAAGUCAAA UUCUUU ACUUUGACCAAGUUUGUAG AAAAU            ACCAA  AAAUA  CU U
GGGAGACAAGGUAUA  AU  CACAAA UCAAAACAG AUUCAGUUU AAGAGA UGAAACUGGUUCAAAUAUC UUUUA            UGGUU  UUUAU  GA U
              GU  UC    G      G       U            U   GU-------------           C-     ACA G

OsmiR438 (ΔG= -59.0)

UGUUUU    CAAACU  UUU          U                        UG .-AUG     GUAU      A
AACG          GGG       UG  UCCCACGCGUUA AGUGAAAACUUUUGGAAU AUGUU UU      GGA     AUAUU \
UUGC          CCU       AC  AGGGUGCGCAAU UCACUUUUGAAAACUUUG UACAG GG      UCU     UAUAG U
       CU----    UCAUCU  UAU          U                        G  GU \ ---  AGGU      U

OsmiR390 (ΔG= -55.9)

U      U  U  A         G              CGAAA
GGUA GGAACAA CC UG AGCUCAGGA GGAUAGCGCCU         U
CCAU UCUUGUU GG AC UCGAGUCCU UCUAUCGCGGA         C
  -      U  U  C         A              UCAAA

OsmiR439a (ΔG= -61.9)

UGA     A      U--             UGU
UACCCUGUCGAAC       CGC  GUUCGACA   GUACCUGUCGAAC   \
GUGGGACAGCUUG       GCG  CAAGCUGU   UAUGGAUAGCUUG   G
                UUG     C      CCC             UUG

OsmiR439b

UU         UG G  U           U
     CCUGUCGAAU   U GU GUUCGAUAGG A
     GGACAGCUUG   G CG CAAGCUGUCC C
     --         UU G  C           C

OsmiR439c

UGA     A      U--             UGU
UACCCUGUCGAAC       CGC  GUUCGACA   GUACCUGUCGAAC   \
GUGGGACAGCUUG       GCG  CAAGCUGU   UAUGGAUAGCUUG   G
                UUG     C      CCC             UUG
```

OsmiR439d

```
CCACC              UCA   UA        U--              UGU
    UACCCUGUCGAAC  CG  GUUCGACA    GUACCUGUCGAAC     \
    GUGGGAUAGCUUG  GC  CAAGCUGU    UAUGGAUAGCUUG      G
-----              UUG  GC         CCC              UUG
```

OsmiR439e

```
CCACC              UGA   A         U--              UGU
    UACCCUGUCGAAC  CGC GUUCGACA    GUACCUGUCGAAC     \
    GUGGGACAGCUUG  GCG CAAGCUGU    UAUGGAUAGCUUG      G
-----              UUG   C         CCC              UUG
```

OsmiR439f

```
ACC                UGA   A         U--              UGU
   UACCCUGUCGAAC   CGC GUUCGACA    GUACCUGUCGAAC     \
   GUGGGACAGCUUG   GCG CAAGCUGU    UAUGGAUAGCUUG      G
---                UUG   C         CCC              UUG
```

OsmiR439g

```
U                  UGA   A         U--              UGU
  CCUGUCGAAC       CGC GUUCGACA    GUACCUGUCGAAC     \
  GGACAGCUUG       GCG CAAGCUGU    UAUGGAUAGCUUG      G
-                  UUG   C         CCC              UUG
```

OsmiR439h

```
ACCACC             UCA   A         U--              UGU
     UACCCUGUCGAAC CGC GUUCGACA    GUACCUGUCGAAC     \
     GUGGGACAGCUUG GCG CAAGCUGU    UAUGGAUAGCUUG      G
------             UUG   C         CCC              UUG
```

OsmiR439i

```
CACC--             UGA   A         U--              UGU
    UACCCUGUCGAAC  CGC GUUCGACA    GUACCUGUCGAAC     \
    GUGGGACAGCUUG  GCG CAAGCUGU    UAUGGAUAGCUUG      G
CAAAUC             UUG   C         CCC              UUG
```

OsmiR439j

```
            C                              U   U   A   C  CA
ACAGGGUACC  UAUCGAACAACUGCGGUUCGACA--GG  ACC AUUGG CUG CA  \
UGUCCAUGG   AUAGCUUGUUGGCGCCAAGCUGU   CC UGG UGAUC GAC GU   C
            -                         \  -   U    G   A   UU
```

OsmiR440 (ΔG= -62.4)

```
         A  UG      C    G  C        C     U    CAA  -    CC
AUUGCU U    UUGGUG UGG CU GUCCUGAUCA UAGGAGAC CUGAU   GC UAGG  U
UAGCGA A    AGCCAC AUC GA CAGGGCUAGU GUCCUCUG GAUUA   UG AUUC  A
         G GU      A    G  A        A     U    ---  U    AA
```

OsmiR396d (ΔG= -92.3)

```
           GCG      C      CA                         G    -U       G  UG
AAAGAUGU      GGCAUG  UUUCCA  GGCUUUCUUGAACUGU  AAC      CGUGGG G  U
UUUCUGCG      CCGUAC  AAAGGU  CCGAAAGAACUUGGUA  UUG      GUACUC U  A
 ---          C       AC                         G    \ -       G  GU
```

OsmiR396e

```
   G   C      CA                         G    .-U       G  UG
GCGG  CAUG  UUUCCA  GGCUUUCUUGAACUGU  AAC      CGUGGG G  U
CGCC  GUAC  AAAGGU  CCGAAAGAACUUGGUA  UUG      GUACUC U  A
 -    C     AC                         G    \ -       G  GU
```

OsmiR441a (ΔG= -67.4)

```
AAAAUAUAUU         G   UU   UA   A                                         A      C          CUAGAU
          AAUUG  UACU   CUC   UUU  ACAAUGUAAGUCAUUUUAGCAUUUC CACAUU  AUAUUGAU           U
          UUAAU  AUGA   GAG   AAA  UGUUACAUUCAGUAAAAUCGUAAAG GUGUAA  UAUAACUA            C
AAAAC-----         G   GG   GC   G                                         G      A          CCAUUA
```

OsmiR441b

```
UUAUCACCACUGACAUA          CC      C          G  A  UU           C        UUA-    AUC
                  CUUCCU  GUUUCA  AAUGUAAGUCAUUUA  UA  UU  CAUAUU  AUAUUGAUG      AUGA   U
                  GAGGGA  CAAAGU  UUACAUUCAGUAAGAU  GU  AA  GUGUAA  UAUAACUAC      UACU   A
AC---------------          UA      A          G  A  GG           A        CAUG    CAG
```

OsmiR441c

```
                                               C           UU                                   GAU
UACUUCCUCUGUUUCAUAAUGUAAGU  AUUUUAGCAUUU   CAUAUUUAUAUUGAUGGUAAUGAAUCUAGAUA      A
AUGAAGGAGGCAAAGUGUUACAUUCA  UAAGAUCGUAAA   GUGUAAAUAUAACUACCAUUACUUAGAUCUGU      U
                                               A           GG                                   AUA
```

OsmiR442 (ΔG= -79.8)

```
       A     A   AUAAAU  AAAA      U-  UA--   UGA  --           CUU           C   AUGAUCGAC      GG    U
CACAUAU  UGGAUAU  AAU     GA   AAUAAC  AAU   UACAGA   CGU  GUAAAUUGCGAGACGAAU  UUAAGCCUAAUUG  UCC          AAUGU  UGC A
GUGUGUA  ACUCAUAA  UUG     CU   UUAUUG  UUG   AUGUCU   GCA  CAUUUGACGCUCUGCUUA  AAUUCGGAUUAAU  AGG          UUACA  AUG C
       A     A   CAU---  GA--      UU  UUUA   UAG  GA           AAU           U   CAGUAAUCGU      A-    A
```

OsmiR443 (ΔG= -74.4)

```
     CAU--        CCC      AG----          A   A                           --    A
CGUCC      AAAAACAAA    AAAAACU      AUGUGAUAUAUC  CA  UACAAUAAAUCUGGAUAGGAG  UCU  U
GCAGG      UUUUUGUUU    UUUUGA       UACACUGUAUAG  GU  AUGUUAUUUAGAUCUAUCUUC  AGA  C
     UUUUU        AUA      CUUAUA          G   C                           AU    C
```

OsmiR445a (ΔG= -141.0)

```
         A   AUGUUG  -   ACGCUAAUUUGGAGUAUUAAACAUA  G    AAA    A   UC  AUGAAA        C            A    C     AU   A   .-AUGAAA  U
UCACAUCG                                                  ACUAAU   AAAAACU  AUU  AUAA       GCUAAU UGCGAGACGAA UUUUU AG CUAAUUA  CCAU AUU        AG U
AGUGUAGC  UACAAU  UGUGAUUAAAUCUCAUAAUUUGUAU  UGAUUA    UUUUGG  UAA    UAUU       UGAUUA GCGCUCUGCUUAGAAAA  UC GAUUAAU  GGUA UAA       UC U
         C   A                          G    AUA    A   GA  GGAACC        A            C    A     GU   C   \------  A
```

OsmiR445b

```
    G         A      -         GAC  AA-   A    UC  AUGAAA       C           A    C    AU   A   -AUGAAA  U
GUCC  UGUCACAUCG  AUGUUG  ACGCUAAUUUAGAGUAUUAAACAUA      UAAU     AAAACU  AUU  AUAA      GCUAAU UGCGAGACGAA UUUUU AG CUAAUUA CCAU AUU        AG U
CAGG  ACAGUGUAGC  UACAAU  UGUGAUUAAAUCUCAUAAUUUGUAU      AUUA     UUUUGG  UAA  UAUU      UGAUUA GCGCUCUGCU GAAAA  UC GAUUAAU GGUA UAA        UC U
    G         C      A          GUA  AUA   A    GA  GGAACC       A           A    C    GU   C  \------   A
```

OsmiR445c

```
cc        A     -                           C   G    AAA       A  UC   AUGAAA         CU                              AU     A   -AUGAAA  U
   GUGUCACAUCG AUGUUG ACGCUAAUUUGGAGUAUUAAA AUA ACUAAU    AAAACU AUU AUAA      GCUAAU GCGAGACGAAUUUUUUAAGCCUAAUUA CCAU AUU       AG U
   UACAGUGUAGC UACAAAU UGUGAUUAAAUCUCAUAAUUU UAU UGAUUA   UUUUGG UAA UAUU      UGAUUA UGCUCUGCUUAGAAAAUUCGGAUUAAU GGUA UAA       UC U
A-         C     A                           A   G    AUA       A  GA   GGAACC         AG                              GU     C   \ ------ A
```

OsmiR445d

```
   -- AA           A    AUU       AAAA           AUG    CCCC---  C    CCCU GA        C    UG  UCUA              A       C    GAUGCU
 UGG  CCAA  UUUAGUCCCUGUCACAUC GAUGUU  ACACUAAUU  GUAUUAAACAUAGACUA  ACAAA  AUU CAUAA  G  UUAAUUCG GAGA  AA  UUGAGUCUAAUUAAUC AUGAUUAGC UAUGU \
 ACC  GGUU  AAAUCAGGGAUGUGUAG CUACAA  UGUGAUUAA  UAUAAUUUGUAUUUGAU  UGUUU  UAA GUAUU  C  GAUUAAGC CUCU  UU  AAUUCGGAUUAAUUAG UAUUAAUUG GUACA  A
    UA  O-          C    AUA       AUC-          GAA    UGAUUAU   C    UACU UC        A    GU  UAAA              O       U    AAUCAC
```

OsmiR445e

```
      G     A     -                           G      AAA       A  UC   AUGAAA         C                  A  C    AU     A  .-AUGAAA U
 GUCC UGUCACAUCG AUGUUG ACGCUAAUUUGGAGUAUAAACAUA ACUAAU  AAAACU AUU AUAA      GCUAAU UGCGAGACGAAUUUUU AG CUAAUUA CCAU AUU       AG U
 CAGG ACAGUGUAGC UACAAAU UGUGAUUAAAUCUCAUAAUUUGUAU UGAUUA  UUUUGG UAA UAUU      UGAUUA GCGCUCUGCUUAGAAAA UC GAUUAAU GGUA UAA       UC U
      G     C     A                           G      AUA       A  GA   GGAACC         A                  C  A    GU     C  \ ------ A
```

OsmiR445f

```
             AAAAC   U    G           A                       G    AAA       A  UC   AUGAAA         C                A    C    AU     A  .-AUGAAA U
 ACAU GGGGCU   UUUU AGUCC UGUCACAUCG AUGUUUG ACGCUAAUUUGGAGUAUUAAACAUA ACUAAU  AAAACU AUU AUAA      GCUAAU UGCGGGACGAAUUUUUU AG CUAAUUA CCAU AUU       AG U
 UUUG CCCUGA   AAAA UCAGG ACAGUGUAGC UACAAAU UGUGAUUAAAUCUCAUAAUUUGUAU UGAUUA  UUUUGG UAA UAUU      UGAUUA GCGCUCUGCUUAGAAAA UC GAUUAAU GGUA UAA       UC U
             U    AU---  U    G           A                       G    AUA       A  GA   GGAACC         A                C    A    GU     C  \ ------ A
```

OsmiR445g

```
     U   G     A     -                             G   AAA       UA  UC   AUGAAA          C           A  CC    AU    A
 AUGAAA U
 UUU AGUCC UGUCACAUCG AUGUUG ACGCUAAUUUGGAGUAUUAAACAUA ACUAAU   AAAAC AUU AUAA      GCUAAU UGCGAGACGAAUUUUUU AG UAAUUA CCAU AUU
 AG U
 AAA UCAGG ACAGUGUAGC UACAAAU UGUGAUUAAAUCUUAUAAUUUGUAU UGAUUA   UUUUG UAA UAUU      UGAUUA GCGUUCUGCUUAGAAAA UC AUUAAU GGUA UAA
 UC U
     U   G     C     A                             G   AUA       UA  GA   GGAACC          A           C  AA    GU    C  \ -----
 A
```

OsmiR445h

```
    U   G     A     -                          G     AAA       A  UC   AUGAAA         C           A  C     AU      A .-AUGAAA U
 UUUU AGUCC UGUCACAUCG AUGUUUG ACACUAAUUUGGAGUAUUAAACAUA ACUAAU  AAAACU AUU AUAA      GCUAAU UGCGAGACGAAUUUUUU AG CUAAUUA CCAU AUU      AG U
 AAAA UCAGG ACAGUGUAGC UACAAAU UGUGAUUAAAUCUCAUAAUUUGUAU UGAUUA  UUUUGG UAA UAUU      UGAUUA GCGCUCUGCUUAGAAAA UC GAUUAAU GGUA UAA      UC U
    U   G     C     A                          G     AUA       A  GA   GGAACC         A           C  A     GU      C  \ ------ A
```

OsmiR445i

```
      UUU   G     A     -                           G   AAA       A  UC   AUGAAA         C             .-AAGCC    AU
 ACUU   AGUCC UGUCACAUCG AUGUUG ACGCUAAUUUAGAGUAUUAAAUAUA ACUAAU  AAAACU AUU AUAA      GCUAAU UGUGAGAUGAAUUUUU       UAAUUA  \
 UGAA   UCAGG ACAGUGUAGC UACAAAU UGUGAUUAAAUUUCAUAAUUUGUAU UGAUUA  UUUUGG UAA UAUU      UGAUUA GCGCUCUGCUUAGAAA       AUUAAU C
      UU-   G     C     A                           G   AUA       A  GA   GGAACC         A             \ ------    AC
```

OsmiR446 (ΔG= -91.4)

```
 AAA-------                                   C   A  AA       C                                       U    GAU
        UAUGUACUUCCUUUGUUUCACAGUGUAAGU AUU UA  AUUCCCA  AUUUAUAUUGAUGUUAAUGAAUCUA AUA      A
        AUAUAUGAGGGAGGCAAAGUGUUACAUUCA UAA AU  UAAAGGGU  UAAGUAUAACUACAAUUAUUUAGAU UGU      U
 CAAGUUCAAG                                   A   G  GG       A                                       C    AUA
```

Figure 11

Predicted fold-back structures of the miR390 from *Arabidopsis* and *Populus*.

*Arabidopsis thaliana* aagctcaggagggatagcgcc

```
        AGAUUGAGU    G     AU       AA           G                  .-U  C
            AGUA AGAA  AGCUAU   AGCUCAGGA  GGAUAGCGCCA       GG  U
            UCGU UCUU  UCGAUA   UUGAGUCCU  CCUAUCGCGGU       CC  C
        ---------  -     CU       CC           A             \ -  A
``` aagctcaggagggatagcgcc

```
    CAAAAAAACAAA-      --       AU U  A        G         ---------       UC
               GUAG  AGAAGA   C GU AAGCUCAGGA  GGAUAGCGCCA         UGAUGA   A
               CAUC  UCUUCU   G UA UUUGAGUCCU  CCUAUCGCGGU         AUUGCU   C
    CCGGAAAAAGUAA    AU       CG U  C        A              UUUUUAUCU      UA
``` aaactcaggatggatagcgcc

```
   --     UUUU---  UU    UA       CCAA    A     U         AAAAAUA    A   G
        CGGCCU    CA  GUAG   AGAAGAG    UGAA  CUCAGGA  GGAUAGCGCCA       GAU AC  A
        GUUGGG    GU  CAUC   UCUUCUU    AUUU  GAGUCCU  CCUAUCGCGGU       CUA UG  A
   GU     UUUUUUU  UU    --       AGAC    C     C         ACUA---    G   U
```

*Populus trichocarpa* aagctcaggagggatagcgcc

```
   UGAUAUGUGCAUA  U         UA       G           AUGA        A   -       GUU    A
UU
\       AGUA  GGGAGGAUCUGU  AGCUCAGGA  GGAUAGCGCC      GCUGAUGAU AG  UUGAU    UG UGGG
        UCGU  UCCUCUUGGAUA  UUGAGUCCU  UCUAUCGCGG      UGAUUACUG UC  AACUA    AC ACUC
A
    UUA----------  -         UC       A           ----        A   U       AU-    A
UA
``` aagctcaggagggatagcgcc

```
    CUUGAUAUAUAGA   U          U  U       G        - A--  GAU--       UG- CU
               AGUA  GGAAGAAUC GU  AAGCUCAGGA  GGAUAGCGCC CU    AG       AACCA    GG  C
               UCGU  UCUUCUUGG CA  UUUGAGUCCU  CCUAUCGCGG GA    UC       UUGGU    UU  U
    CA----------   -          U  U       A        U CUA   AGUUU       UUA UU
``` aagctcaggagggatagcgcc

```
    G--         UA       G           GAGC        AAAGUCUA---        U    UU
        GGAGAAUCUGU  AGCUCAGGA  GGAUAGCGCCAU    AUGAC                 UGUU GAG   \
        CCUCUUGGGUA  UUGAGUCCU  UCUAUCGCGGUG    UACUG                 ACAA CUC    A
    AUU         UC       A           AC--        ACCUAACUAAA         -    UA
``` aagctcaggagggatagcgcc

```
                AUAGAAA    U          UCU  U           G              - A      AAU------
CU
                       AGUA GGAAGAA      GU AAGCUCAGGA GGAUAGCGCC CU AGGAU             CAUGGG
\
                       UCGU UCUUCUU      UA UUUGAGUCCU CCUAUCGCGG GA UCUUA             GUAUUU
C
        ACCA---    -          CGU  C           A              U   C      GUUUUUGGU
UU
``` aaactcaggatggatagcgcc

```
           AA--       CCA  A  A        U            A    UA  CAAA       AAUAAAA
             GAAGAA     GU AA CUCAGGA GGAUAGCGCC CUGA  GU    AACCA             \
             CUUCUU     CA UU GAGUCCU CCUAUCGCGG GAUU  UA    UUGGU             A
           AUAC       AGA  A  C        C            -    CC  ----       ACCCGAG
``` aaactcaggatggatagcgcc

```
           GGAGCU      GCAA       GCAAUG  A        U          A    ---        AAAACCACAU
             GGUA       GAAGAA      AA CUCAGGA GGAUAGCGCC CUGAG    AAUCA              A
             UCAU       CUUCUU      UU GAGUCCU CCUAUCGCGG GAUUC    UUAGU              A
           U-----      AC--       AGACAA  C        -          CUA            ACCCGAGAAA
```

Figure 12

Predicted fold-back structures of miR437 from maize, sugarcane and *Sorghum*.

Maize

```
         C    C    U                      - C   CC        U-      CAGAAA      C        CCAU      C  C  G    U
   UAUUUUAGC UUG CCUAA UUAGACUUCUCUA CU UGA AUGUUUAU AAAAAUG      CAUCUA AAUAUUAAA    UAGAUA AC AU AAA \
   GUAAAAUUG AAC GGGUU AGUUUGAAGAGAU GA ACU UACAAAUA UUUUUAU      GUAGAU UUAUAGUUU    AUUUGU UG UA UUU A
         A    A    C                      C A   U-        UC      ACAAUC      U        ----      A  A  G    U
```

Sugarcane

```
         --   C  GU  A     ACUAAACUUC        CC      C               A        UGCACCAAA-     G  .-UAUCAAACUAGUUCCAUUAAA
   UC
     UACUCU CUGUU CAA  UAU GUUUACU        AGCUUUGUC AAGUCAAAC UCUCUAACUUUGAUCAAGUUU UAGAAAAA        AUCUA AA                UUC
   \
     AUGAGG GGCAA GUU  AUA CAAGUGA        UCGAAACAG UUCAGUUUG AGAGAUUGAAACUAGUUCAAA AUCUUUUU        UAGAU UU                AAG
   C
         GC    A  UG  A     AA--------       NA      A               A        UAUAUAAUAG     G  \  --------------------
   UA
```

Sorghum

```
                 U          A    U      -     C  C             A       - C  C     -     C  .-UACAAA     U
   UUCCAAAAUGU GGUUGUUUU GUUUU GUCAUAAGU AAAUU UCUC AACUUUGACCAAGUUU UAGAAAA UA AC AACAU GGCAA AUC         AUGAAA G
   GAGGUUUUACA CCAGCAAAA CAAAA UAGUAUUCA UUUGA AGAG UUGAAAUUGGUUCAAA AUCUUUU AU UG UUGUA UCGUU UGG         UGCUUU A
                 U          C          G    A             C       U A A     G     A  \  ------         A
```

Figure 13

Predicted fold-back structures of the putative miRNA precursors from rice (see Table 5).

P18-F1 (ΔG= -63.3)

```
UGUUAAACGGCAC       U     A-      U                     A        UGG----      U-       UA
             GGUUU CUUGG   UCUCUC CUCCCUUGAAGGCU UCUCA              AGGU   UGAUG     \
             CCGAA GAACC   AGAGAG GAGGGGCUUCCGA AGAGU               UCCG   GUUAC     C
UGACA--------       C     GA      -                     A        CAAAGAA      UU       CA
```

P20-A11 (ΔG= -114.1)

```
   A   A  C                    A         C  A      C      UG                      UG     GGU
AG UUU CU CGGUCCAACAAAAAGUA CUCGAGGUA CG UACCUC CGGUAC AAAU  UUUCCGAUCGUUGGAUCUAGC   GGUG    \
UC AAA GA GCCAGGUUGUUUUUCAU GAGCUCCAU GC AUGGAG GCCAUG UUUA  AAAGGCUAGCAACCUAGAUUG   CUAC    U
   A   A  A                    A         A  C      C      U  GU                      --     GGG
```

P83-E9 (ΔG= -201.3)

```
AAU   C       A  AA          C    G       A          C             C      UCC         A  A         C  A  .-C    A- A  A --       A
   AGCU UAUAUAUG CAC  AAUUUGACAAUU ACCC UUCCGAAAACUA UUUCGCAAAUGAACCGCGGC AAAAUUUAUUU AAAAAUG   CUUUUGUUUAGCGCCA AUC UAUGGCGUUGAAC UA ACA   CUCAGC  CC CGUC AC  UGGCGCUG U
   UUGA GUAUAUAU GUG  UUAAACGUUAAA UGGG AAGGCUUUUGAU AAAGCGUUUACUUGGCGCCG UUUUGAAUAAA UUUUUAC   GAAAACAAGUCGCGCU UAG AUACUGUGACUUG AU UGU   GAGUCG  GG GUAG UG  ACCGUGAC U
--- A       C  AA         C    A       C          A             A      UGA         A  C         A  C  \-    GA - G CC          A
```

P92-A7 (ΔG= -74.8)

```
             A                G   - CC   U   UCC     ACU--           -CAAUAC           AUAUA  A  UAU     G
GAUGCUUCUUUC UCCUAAAAUAUAAGCA UUUUAG AC UGACA AGUU GAUAU      ACUUUGAU           AAUAUACAAU      UAU UA   AUAUA U
CUAUGAAGGAGG AGGGUUUAUAUUUGU AAAAUU UG ACUGU UCAG UUGUA      UGAACUG           UUAUAUGUUG      AUA AU   UGUAU A
             C                A   G UC   -   U--     AAAAU    \ ------           AAAA-  A  UU-     A
```

P101-H12 (ΔG= -160.0)

```
CA             AAUA                   C                                                               CU
  UGUGGCUCGCAUGCUUA    ACUAACGGCAUAAUUAGAUCACUUGAUGA GACGUAUAUCGGUGUUCGCUAUAUAUACUAUCUACUGGUAAGUAUAU    \
  ACACCGAGCGUACGAAU    UGAUUGCCGUAUUAAUUUAGUGAACUACU CUGCGUAUAGCCACAAGUGAUAUAUAUGAUAGAUGACCAUUCAUAUA    U
--             ----                   A                                                               AU
```

CLONING AND CHARACTERIZATION OF MICRORNAS FROM RICE

CROSS-REFERENCE TO RELATED APPLICATIONS

This application claims priority to U.S. patent application 60/666,780, filed Mar. 30, 2005, the contents of which are incorporated by reference in the entirety.

STATEMENT AS TO RIGHTS TO INVENTIONS MADE UNDER FEDERALLY SPONSORED RESEARCH AND DEVELOPMENT

This work was supported by National Institutes of Health grant R01GM0707501 and National Science Foundation grant IBN-0212346.

BACKGROUND OF THE INVENTION

MicroRNAs (miRNAs) are short, endogenous noncoding RNAs found in animals (Lee, R. C. et al., *Cell* 75:843-854 (1993); Wightman, B. et al., *Cell* 75:855-862 (1993); Lagos-Quintana, M. et al., *Science* 294:853-858 (2001); Lagos-Quintana, M. et al., *Curr. Biol.* 12:735-739 (2002); Lagos-Quintana, M. et al., *RNA* 9:175-179 (2003); Lau, N. C. et al., *Science* 294:858-862 (2001); Lee, R. C. et al., *Science* 294:862-864 (2001); Lim, L. P. et al., *Science* 299:1540 (2003a); Lim, L. P. et al., *Genes Dev.* 17:991-1008 (2003b); Mourelatos, Z., et al., *Genes Dev.* 16:720-728 (2002); Aravin, A. et al., *Dev. Cell* 5:337-350 (2003); Ambros, V. et al., *Curr. Biol.* 13:807-818 (2003a); Dostie, J. et al., *RNA* 9:180-186 (2003); Grad, Y. et al., *Mol. Cell* 11:1253-1263 (2003)), plants (Reinhart, B. J. et al., *Genes Dev.* 16:1616-1626 (2002); Llave, C. et al., *Plant Cell* 14:1605-1619 (2002a); Park, W. et al., *Curr. Biol.* 12:1484-1495 (2002); Mette, M. F. et al., *Plant Physiol.* 130:6-9 (2002); Palatnik, J. F. et al., *Nature* 425:257-263 (2003); Floyd, S. K. et al., *Nature* 428:485-486 (2004); Jones-Rhoades, M. J. et al., *Mol. Cell* 14:787-799 (2004); Sunkar, R. et al., *Plant Cell* 16:2001-2019 (2004); Wang, J-F. et al., *Nucleic Acids Res.* 32:1688-1695 (2004a); Wang, X. J. et al., *Genome Biol.* 5:R65 (2004b); Adai, A. et al., *Genome Res.* 15:78-91 (2005)), and the Epstein-Barr virus (Pfeffer, S. et al., *Science* 304:734-736 (2004)). In both animals and plants, the majority of the miRNA genes exists as independent transcriptional units and they are transcribed by RNA polymerase II into long primary transcripts (termed pri-miRNAs) (Bartel, D. P. *Cell* 116:281-297 (2004); Parizotto, E. A. et al., *Genes Dev.* 18:2237-2242 (2004); Kurihara, Y. et al., *Proc. Natl. Acad. Sci. USA* 101:12753-12758 (2004)). In animals, pri-miRNAs are trimmed in the nucleus to generate ~70 nt miRNA precursors (pre-miRNAs) with fold-back structures by a multi-protein complex called microprocessor in which Drosha (an RNase III-like enzyme) and Pasha (a double-stranded RNA binding protein) are critical components (Lee, Y. et al., *Nature* 425:415-419 (2003); Denli, A. H. et al., *Nature* 432:231-234 (2004)). The pre-miRNAs are exported to the cytoplasm and subsequently cleaved by another RNase III-like enzyme called Dicer to generate mature miRNAs (Bernstein, E. et al., *Nature* 409:363-366 (2001)). However, the *Arabidopsis* genome does not appear to encode a Drosha ortholog, and it seems that the plant nuclear-localized Dicer homolog is likely to have Drosha function (Kurihara, Y. et al., *Proc. Natl. Acad. Sci. USA* 101:12753-12758 (2004)). Many miRNAs are conserved between species—often over wide evolutionary distances. For example, AthmiR166 is conserved in all lineages of land plants, including bryophytes, lycopods, ferns and seed plants (Floyd, S. K. et al., *Nature* 428:485-486 (2004)), and the *Caenorhabditis elegans* miRNA, let-7, is conserved in human, *Drosophila*, and eleven other bilateral animals (Pasquinelli, A. E. et al., *Nature*. 408:86-89 (2000)); but others are only conserved between more closely related species such as *C. elegans* and *C. briggsae* (Ambros, V. et al., *Curr. Biol.* 13:807-818 (2003a); Bartel, D. P. *Cell* 116:281-297 (2004)). miRNAs down-regulate the expression of specific mRNA targets, either by directing the cleavage of mRNAs or interfering with translation (Carrington, J. C. et al. *Science* 301:336-338 (2003); Bartel, D. P. *Cell* 116:281-297 (2004); Ambros, V. *Nature* 431:350-355 (2004)).

miRNAs have been identified by cloning and by computational approaches tailored to the key features of lin-4 and let-7, the 2 founding members of miRNAs from *C. elegans*, which include a fold-back hairpin RNA precursor coupled with evolutionary conservation (Ambros, V. et al., *RNA* 9:277-279 (2003b)). It was estimated that miRNA genes represent 1% of the expressed genome in complex organisms such as worms, flies and humans (Lai, E. C. *Curr. Biol.* 13:R925-R936 (2003); Lim, L. P. et al., *Genes Dev.* 17:991-1008 (2003b); Bartel, D. P. *Cell* 116:281-297 (2004)). However, recent computational predictions have raised the number of miRNAs significantly in primates by comparative analysis of the human, mouse and rat genomes (Berezikov, E. et al., *Cell,* 120:21-24 (2005)). The identification of the entire set of miRNAs and their target genes from model organisms is of fundamental importance to understand regulatory networks and gene silencing mechanisms.

Rice is the world's most important crop, as measured by the portion of calories it provides to the human diet. It is an established model system for monocots that include all cereals. Rice is the only monocot species with a fully sequenced genome. The availability of the complete genome sequence of rice allowed the in silico identification of 20 families of rice miRNAs based on conservation of sequences with *Arabidopsis* miRNAs (Reinhart, B. J. et al., *Genes Dev.* 16:1616-1626 (2002); Park, W. et al., *Curr. Biol.* 12:1484-1495 (2002); Jones-Rhoades, M. J. et al., *Mol. Cell* 14:787-799 (2004); Sunkar, R. et al., *Plant Cell* 16:2001-2019 (2004); Bonnet, E. et al., *Proc. Natl. Acad. Sci. USA*. 101:11511-11516 (2004); Wang, J-F. et al., *Nucleic Acids Res.* 32:1688-1695 (2004a); Adai, A. et al., *Genome Res.* 15:78-91 (2005)). In addition to finding conserved miRNAs, cloning approaches revealed *Arabidopsis* miRNAs that are not conserved in rice. At least four well-characterized *Arabidopsis* miRNAs, miR158, miR161, miR163 and miR173 do not have homologs in rice (Jones-Rhoades, M. J. et al., *Mol. Cell* 14:787-799 (2004)). Another miRNA (miR403) has been found to be conserved between *Arabidopsis* and *Populus* while its counterpart could not be identified in rice (Sunkar, R. et al., *Plant Cell* 16:2001-2019 (2004)). Recently, evidence was shown that the non-conserved miR161 and miR163 from *Arabidopsis* may have evolved by inverted duplication of their target genes (Allen, E. et al., *Nature Genet.* 36:1282-1290 (2004)). Additionally, Berezikov, E. et al., *Cell,* 120:21-24 (2005)) have predicted lineage specific miRNAs in mammalian and non-mammalian animal species. Taken together, these observations support the notion that rice may express monocot- and/or rice-specific miRNAs.

The present study was undertaken to identify new miRNAs that are difficult to predict in silico and verify previously predicted miRNAs from rice. Sequencing of small RNA libraries and subsequent analysis led to the identification of 14 new miRNAs. These new miRNAs from rice form 14 families, 13 of which are new and not present in *Arabidopsis*.

Furthermore, we confirmed the existence of 15 of the 20 conserved families of miRNAs that were predicted previously. Based on sequence complementarity to miRNAs, we were able to predict 46 rice genes as putative targets of the new miRNAs. These predicted targets include not only transcription factors but also other genes involved in diverse physiological processes.

BRIEF SUMMARY OF THE INVENTION

MicroRNAs (miRNAs) are a growing family of small non-coding RNAs that down-regulate gene expression in a sequence-specific manner. The identification of the entire set of miRNAs from a model organism is a critical step towards understanding miRNA-guided gene regulation. Rice and *Arabidopsis*, two plant model species with fully sequenced genomes, are representatives of monocotyledonous and dicotyledonous flowering plants, respectively. Thus far, experimental identification of miRNAs in plants has been confined to *Arabidopsis*. Computational analysis based on conservation with known miRNAs from *Arabidopsis* has predicted 20 families of miRNAs in rice. To identify miRNAs that are difficult to predict in silico or not conserved in *Arabidopsis*, we generated 3 cDNA libraries of small RNAs from rice shoot, root and inflorescence tissues. We identified 35 miRNAs, of which 14 are new and these define 13 new families. Thirteen of the new miRNAs are not conserved in *Arabidopsis*. Four of the new miRNAs are conserved in related monocot species but not in *Arabidopsis*, which suggests that these may have evolved after the divergence of monocots and dicots. The remaining 9 new miRNAs appear to be absent in the known sequences of other plant species. Most of the rice miRNAs are expressed ubiquitously in all tissues examined, while a few display tissue-specific expression. We predicted 46 genes as targets of the new rice miRNAs, and 16 of these predicted targets encode transcription factors and other target genes appear to have roles in diverse physiological processes. Four target genes have been experimentally verified by detection of miRNA mediated mRNA cleavage. Our identification of new miRNAs in rice suggests that these miRNAs may have evolved independently in rice or may have been lost in other species.

BRIEF DESCRIPTION OF THE DRAWINGS

FIG. 2. OsmiR396d is a unique member of the previously predicted OsmiR396 family in rice. Sequence alignment of miR396d (SEQ ID NO:2) and predicted members of OsmiR396 family (SEQ ID NOS:74 and 75). OsmiR399 family=SEQ ID NOS:34 and 76-81.

FIG. 4. The miR444 family is conserved in monocots. (A). Alignment of miR444 sequence from rice (SEQ ID NO:12) with the predicted homologs in wheat (SEQ ID NO:12), barley (SEQ ID NO:12), maize (SEQ ID NO:83), sorghum (SEQ ID NO:83) and sugarcane (SEQ ID NO:83). (B). Predicted fold-back structures of miR444 precursors from rice, wheat, barley, maize, sorghum and sugarcane (SEQ ID NOS: 84-89).

FIG. 8. OsmiR439 (SEQ ID NO:7) is predicted to target 3 sites within the ORF of its target gene, 11667.m02576 (SEQ ID NOS:91 and 92). Numbers represent the position of target sites in the ORF. Amino acid sequence corresponding to the target nucleotide sequence is shown.

FIG. 10. Predicted fold-back structures of the new miRNA precursors from rice (SEQ ID NOS:100-131).

FIG. 11. Predicted fold-back structures of miR390 from *Arabidopsis* (SEQ ID NOS:133, 134 and 136) and *Populus* (SEQ ID NOS:137-142). miRNAs (reverse complement form)=SEQ ID NOS:132 and 135).

FIG. 12. Predicted fold-back structures of miR437 from maize, sugarcane, and *Sorghum* (SEQ ID NOS:143-145).

FIG. 13. Predicted fold-back structures of the putative miRNA precursors from rice (Table 5) (SEQ ID NOS:146-150).

DEFINITIONS

Figure 1:
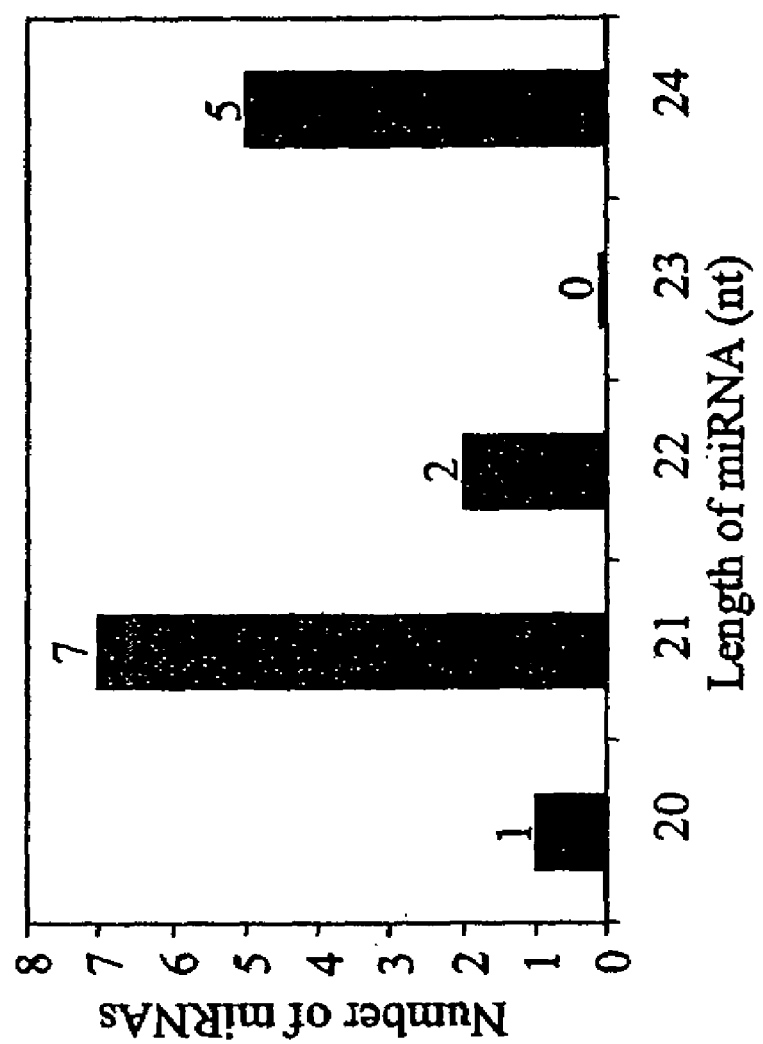
FIG. 1. Size distribution of new miRNAs cloned from rice.

As used in this application, the term "expression cassette" refers to any recombinant expression system for the purpose of expressing a nucleic acid sequence of the invention in vitro or in vivo, constitutively or inducibly, in any cells, including, in addition to plant cells, prokaryotic, yeast, fungal, insect, or mammalian cells. The term includes linear or circular expression systems. The term includes all vectors. The cassettes can remain episomal or integrate into the host cell genome. The expression cassettes may have the ability to self-replicate or may not, i.e., drive only transient expression in a cell. The term includes recombinant expression cassettes that contain only the minimum elements needed for transcription of the recombinant nucleic acid.

As used herein, the term "promoter" includes all sequences capable of driving transcription of a coding sequence in a plant cell. Thus, promoters used in the constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation.

These cis-acting sequences typically interact with proteins or other biomolecules to carry out (turn on/off, regulate, modulate, etc.) transcription. Promoters can be constitutive or inducible.

The term "plant" includes whole plants, shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Optimal alignment of sequences for comparison may be conducted by the local homology algorithm of Smith and Waterman Add. APL. Math. 2:482 (1981), by the homology alignment algorithm of Needle man and Wunsch *J. Mol. Biol.* 48:443 (1970), by the search for similarity method of Pearson and Lipman *Proc. Natl. Acad. Sci.* (U.S.A.) 85: 2444 (1988), by computerized implementations of these algorithms (GAP, BESTFIT, BLAST, FACTS, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 70% sequence identity, at least 80% sequence identity, preferably at least 85%, more preferably at least 90%, 93% and most preferably at least 95%, or 97% compared to a reference sequence using the programs described herein; preferably BLAST using standard parameters, as described below. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%, preferably at least 60%, 70%, 80% or more preferably at least 90%, and most preferably at least 95%. Polypeptides that are "substantially similar" share sequences as noted above except that residue positions that are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

For the purposes of this disclosure, stringent conditions for hybridizations are those including at least one wash in 0.2× SSC at 63° C. for 20 minutes, or equivalent conditions. Moderately stringent conditions include at least one wash (usually 2) in 0.2×SSC at a temperature of at least about 50° C., usually about 55° C., for 20 minutes, or equivalent conditions.

All publications and patent applications cited in this specification are herein incorporated by reference as if each individual publication or patent application were specifically and individually indicated to be incorporated by reference.

DETAILED DESCRIPTION

I. Introduction

The present invention is based, at least in part, on the identification of new miRNAs in rice. The nucleic acids of the invention can be used to control gene expression in plants. In some embodiments, the expression cassettes encoding the miRNAs of the invention are prepared and introduced into plants. The encoded miRNAs then control expression of the endogenous target genes. Alternatively, one can modify the target gene so as to render it miRNA-resistant by modifying the sequence to decrease or inhibit pairing with the miRNA. The modifications will typically be selected such that the sequence of the encoded protein is not altered. The modified target gene can be incorporated into an expression cassette and introduced into a plant. Alternatively, an endogenous target gene can be modified using known techniques (e.g., homologous recombination).

More specifically, the present inventors discovered 14 new miRNAs in rice. These new miRNAs form 14 families, 13 of which are new and not found in *Arabidopsis*. In addition, 46 rice genes have been identified as putative targets of the new miRNAs, based on their sequence complementarity to the miRNAs.

II. General Description of Techniques Used in the Invention

Standard techniques in the field of molecular genetics are useful for the present invention. Basic texts disclosing the general methods such as cloning, nucleic acid sequencing, detection of nucleic acids, and gene transfer and expression, include, e.g., Sambrook and Russell, *Molecular Cloning: A Laboratory Manual* 3d ed. (2001); Kriegler, *Gene Transfer and Expression: A Laboratory Manual* (1990); and Ausubel et al., *Current Protocols in Molecular Biology* (1994).

For nucleic acids, sizes are given in either kilobases (Kb) or base pairs (bp). These are estimates derived from agarose or polyacrylamide gel electrophoresis, from sequenced nucleic acids, or from published DNA sequences. For proteins, sizes are given in kilo-Daltons (kD) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage and Caruthers, *Tetrahedron Letters*, 22: 1859-1862 (1981), using an automated synthesizer, as described in Van Devanter et al., *Nucleic Acids Res.*, 12: 6159-6168 (1984). Purification of oligonucleotides is by either native polyacrylamide gel electrophoresis or by anion-exchange chromatography as described in Pearson & Reanier, *J. Chrom.*, 255:137-149 (1983). The sequence of the cloned genes and synthetic oligonucleotides can be verified aftercloning using, e.g., the chain termination method for sequencing double-stranded templates of Wallace et al., *Gene* 16:21-26 (1981).

III. Gene Transfer Techniques

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al., *Embo J.* 3:2717-2722 (1984). Electroporation techniques are described in Fromm et al., *Proc. Natl. Acad. Sci. USA* 82:5824 (1985). Ballistic transformation techniques are described in Klein et al., *Nature* 327:70-73 (1987).

*Agrobacterium tumefaciens*-mediated transformation techniques, including disarming and use of binary vectors, are well described in the scientific literature. See, for example, Horsch et al., *Science* 233:496-498 (1984), and Fraley et al., *Proc. Natl. Acad. Sci. USA* 80:4803 (1983).

Transformed plant cells that are derived by any of the above transformation techniques can be cultured to regenerate a whole plant that possesses the transformed genotype and thus the desired phenotype. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124-176, Mac-Millilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee et al., *Ann. Rev. of Plant Phys.* 38:467-486 (1987).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The expression cassettes of the invention can be used to confer a desired trait on essentially any plant. Thus, the invention has use over a broad range of plants, including species from the genera *Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna*, and, *Zea*.

EXAMPLES

The following examples are provided for the purpose of illustration and not limitation. Those of skill in the art will readily recognize a variety of non-critical parameters that could be changed or modified to yield essentially the same or similar results.

RESULTS

Identification of 13 New Families of Rice MiRNAs

Because the available computational approaches can only identify miRNAs that are conserved between *Arabidopsis* and rice, a cloning approach was employed to identify rice miRNAs that may not be conserved or may have atypical features (Dugas, D. V. et al., *Curr. Opin. Plant Biol.* 7:512-520 (2004)). To this end, we generated 3 independent small RNA libraries from rice in the size range of 18-26 nt, from the shoots and roots of seedlings and inflorescence tissues of adult plants (*Oryza sativa* spp *japonica* cv. Nipponbare). Small RNAs were isolated by size fractionation and ligated to 5' and 3' adapters, cloned and sequenced. A total of ~10,000 clones were sequenced (about ⅓ from each library), of which ~5000 small cDNA sequences were between 18 and 26 nt in length. The remaining sequences had either shorter fragments or self-ligated adapters. BLASTN searches revealed that 97% of these sequences have at least one match in the rice nuclear genome sequence Version 3 annotated by TIGR (web site is tigr.org). The remaining 3% did not have a match and were not analyzed further. The lack of a match of these sequences may be due to unfinished regions in the rice genome sequence, sequencing errors or other possibilities. Several clones were mapped to chloroplast or mitochondrial genomes and may represent either degradation or possibly regulatory products of organellar RNAs. The largest class of cloned RNAs represents fragments of abundant noncoding RNAs (rRNA, tRNA, snRNA and snoRNA) as determined by BLASTN searches against the Rfam database. A small fraction represents mRNA breakdown products from rice. The remaining sequences constitute miRNAs (Table 1 and Table 2) and endogenous siRNAs (data not shown). For 95% of the endogenous siRNAs, we could not be detected their expression on small RNA blots.

MicroRNAs were distinguished from endogenous siRNAs on the basis of the ability of the miRNA surrounding sequences to adopt a hairpin structure (FIG. 10). This analysis revealed that we had cloned 35 rice miRNAs. We also found one small RNA sequence that corresponds to OsmiR399g*. Sequence similarity searches against the central miRNA registry (web site is sanger.ac.uk/Software/Rfam/mirna/search.shtml) showed that 14 of the miRNAs are new (Table 1). The remaining 21 (belonging to 15 families) were identical with previously predicted miRNAs in rice (Table 2). The newly identified 14 miRNAs correspond to 34 loci. These new miRNAs belong to 2 predominant size classes: 21 and 24 nt in length (FIG. 1). Nine of the 14 newly identified miRNAs begin with a 5' U which is a characteristic feature of miRNAs (Table 1). All 14 new miRNAs are perfectly conserved in Indica rice (*Oryza sativa* spp *indica*)

One of the newly identified miRNAs is represented by 2 genomic loci, OsmiR396d and OsmiR396e, and is a member of previously predicted OsmiR396 family in rice (Table 1 and FIG. 2). OsmiR396d was represented by 10 clones in our libraries and differed slightly in sequence from that of predicted OsmiR396 (FIG. 2). The predicted OsmiR396 has 3 genomic loci (OsmiR396a, b and c) and is represented by 2 members (Jones-Rhoades, M. J. et al., *Mol. Cell* 14:787-799 (2004)). OsmiR396d differs from these two members by the presence of an additional nucleotide "G" between positions 8 and 9. Using a specific probe, we detected the expression of miR396d in rice and maize but not in *Arabidopsis* (FIG. 7A). Although cross-hybridization often occurs between members in the same miRNA family, this is prevented by the presence of an additional nucleotide in the middle of miR396d. Consistent with the absence of a signal in the *Arabidopsis* Northern blot, the miR396d sequence is not present in the *Arabidopsis* genome. OsmiR396d sequence and the secondary structure of its precursor sequences are conserved in barley, another monocotolydonous plant (data not shown).

Our sequence analysis indicated that we also identified a new miRNA that is conserved between monocots and dicots. We identified miR390 in rice through cloning, whereas the *Arabidopsis* counterpart was predicted through recent computational approaches (Bonnet, E. et al., *Proc. Natl. Acad. Sci. USA.* 101:11511-11516 (2004); Wang, X. J. et al., *Genome Biol.* 5:R65 (2004b)). miR390 is represented by one member with one locus in rice (Table 1) while in *Arabidopsis* and *Populus* it is represented by 2 members with 3 and 6 loci, respectively (FIG. 11).

Genomic Organization of the New Rice miRNAs

Genomic locations of the new miRNA genes in rice are shown in Table 1. In total, the 14 newly identified miRNAs correspond to 34 loci. Hairpin structures can be predicted for all these 34 loci using miRNA surrounding sequences (FIG. 10). Ten of these are encoded by single copy miRNA genes, whereas the other 4 (miR439, miR396d, miR441 and miR445) have multiple loci in the genome (Table 1). The exact origins of miRNAs corresponding to multiple genomic loci cannot be assigned unambiguously, and some of the loci could be pseudogenes. Our analysis of the genomic positions of the new miRNA genes shows that the majority localizes to intergenic regions (25 out of 34 loci). However, 7 correspond to introns of protein-coding genes in either the sense (6) or antisense (1) orientation (Table 1). Our characterization of intronic origins of miRNAs was based on latest annotation of *Oryza sativa* spp. *japonica* genome (version 3.0). Two miR-NAs (miR439 and miR445) map to both intergenic and intronic locations. Two (miR435 and miR440) are derived from introns only. Another 2 miRNAs (miR436 and miR444) originate from the exons of protein-coding genes in the sense polarity (Table 1).

Biogenesis of OsmiR436 and OsmiR444

In general, most of the 20-25-nt mature miRNAs are processed from a 70-300 nt precursor forming a hairpin structure that contains mature miRNA in either of its arms. Two miR-NAs, miR436 and miR444, were mapped to the exons of the protein-coding genes J023035E19 (AK120922) and J033125N22 (AK103332), respectively, in the sense polarity (Table 1). The existence of these processed transcripts is supported by expression data (Kikuchi et al., 2003). Both of the precursor transcripts can form hairpin structures, and the miRNAs were detected on small RNA blots as discrete bands, suggesting that these are not non-specific degradation products.

Figure 3:
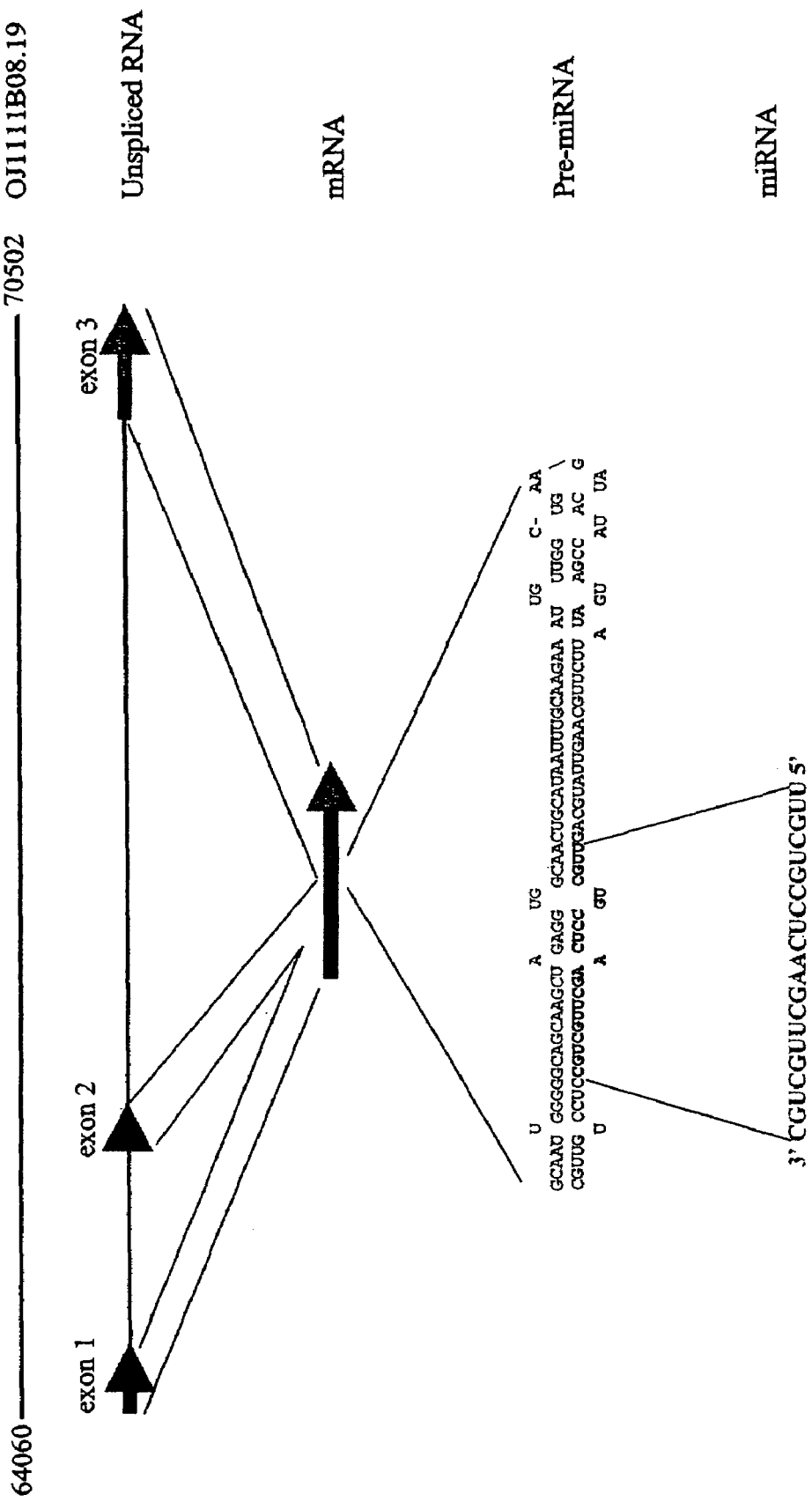
FIG. 3. Schematic representation of the biogenesis of OsmiR444 (SEQ ID NO:12). Its hairpin structure (SEQ ID NO:82) requires parts of exon 2 and exon 3 of the host transcript J033125N22.

The biogenesis of OsmiR444 and OsmiR436 is unusual, because the fold-back structure could not be predicted directly from the genomic sequence surrounding the miRNA. A hairpin structure can be predicted for a processed transcript (part of exons 2 and 3 sequences) but not with the genomic sequence, which suggests that the presence of an intron prevented the identification of a fold-back structure in the genomic locus of miR444 (FIG. 3). The mature miR444 resides in the $3^{rd}$ exon of the gene J033125N22. The ORF of this gene is predicted to code for an unknown protein of 50 amino acids. It is possible though that the processed mRNA is just a pri-miRNA444 transcript and does not code for a protein.

miR444 is conserved in monocots such as wheat, barley, maize, sorghum and sugarcane but not in *Arabidopsis* (FIG. 4A). The precursor sequences from all these plants can form a hairpin structure (FIG. 4B). Unlike the situation in rice, the corresponding miRNA precursor fold-back structures can be predicted from the un-spliced genomic sequences from the available sequences of other monocots.

Figure 5:
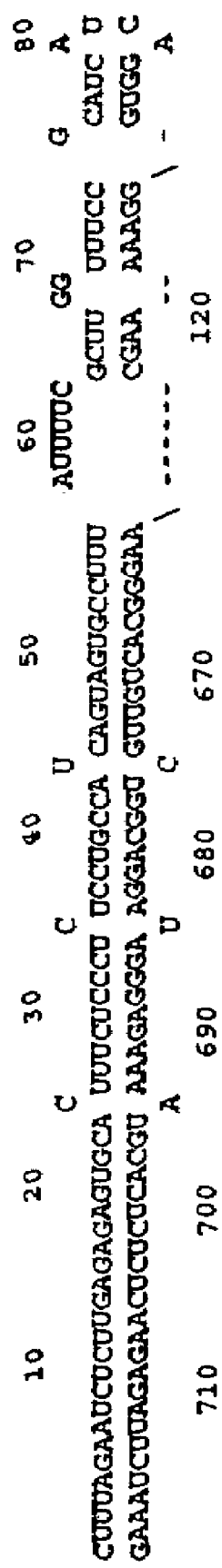
FIG. 5. Predicted fold-back structure of OsmiR436 precursor (SEQ ID NO:90). The fold-back structure was predicted with use of a 720-bp processed transcript. Protruding stem-loops in the 3' arm of the hairpin are indicated by the \ sign.

Similarly, OsmiR436 also resides in the same polarity of a processed transcript (J023035E19), and only the processed transcript can form a hairpin structure. The mature miR436 resides in the $3^{rd}$ exon of the gene J023035E19. The predicted fold-back structure requires a very long part (720 nt; exons 3 to 9) of the processed transcript (FIG. 5) because of the presence of stem-loop structures protruding from the 3' arm of the hairpin structure.

Expression Patterns of Rice miRNAs

Figure 6:
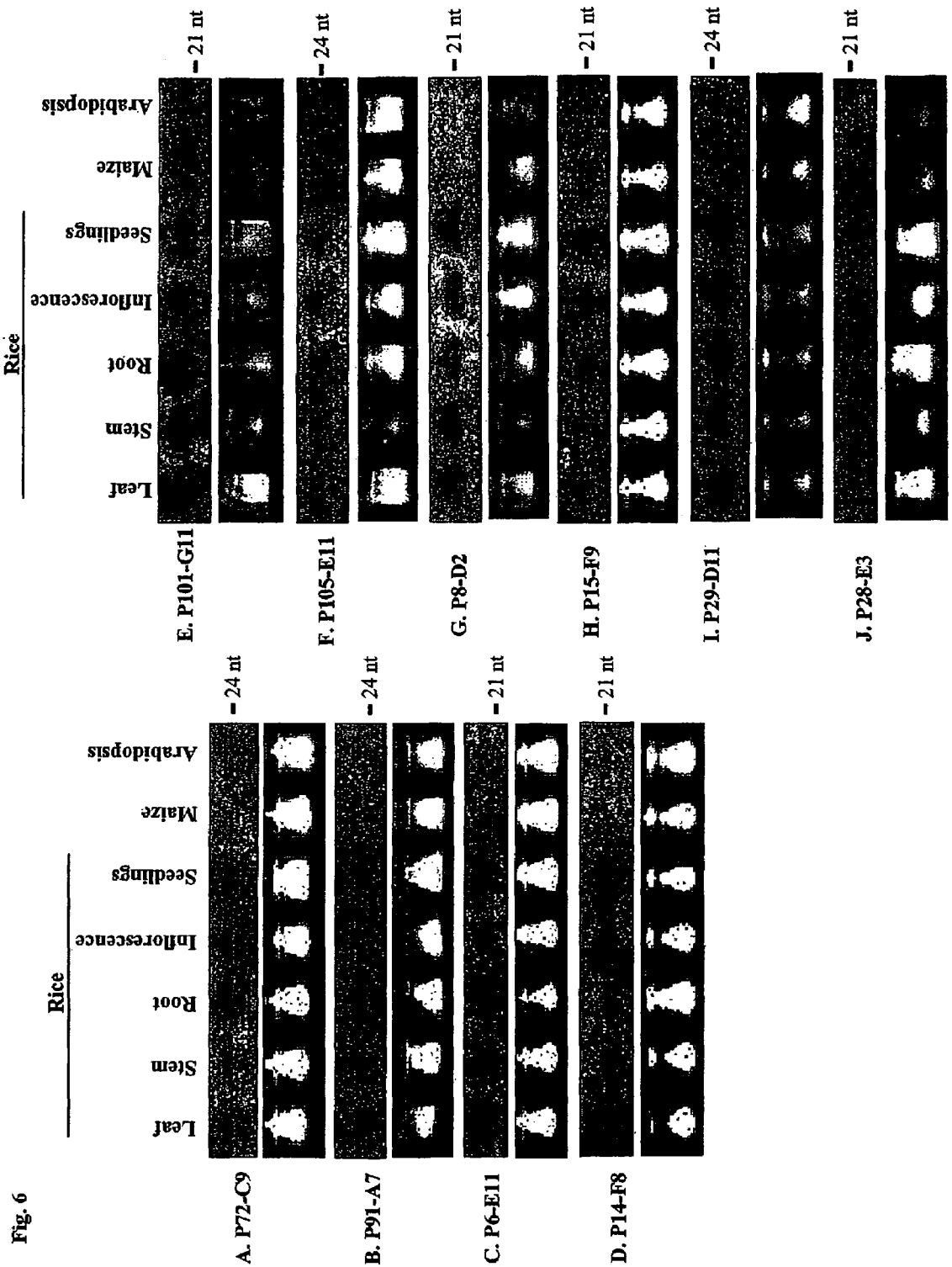
FIG. 6. Expression patterns of miRNAs cloned from rice. Northern blots of total RNA isolated from different tissues were probed with labeled oligonucleotides. The blots also included RNA from maize and *Arabidopsis*. The tRNA and 5S rRNA bands were visualized by ethidium bromide staining of polyacrylamide gels and served as loading controls. Labelled RNA oligonucleotide was used as a size marker and the position was indicated.
Figure 7:
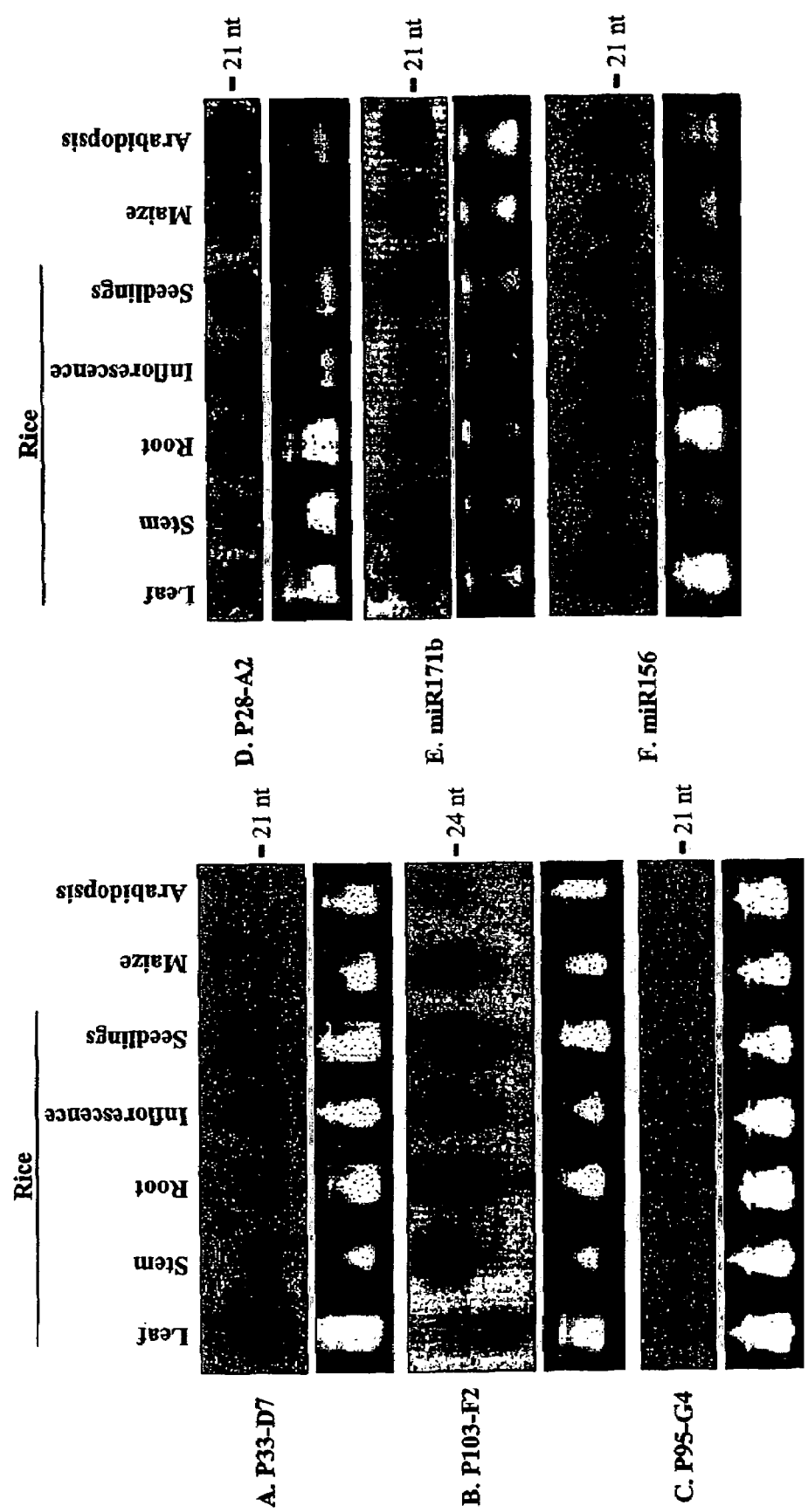
FIG. 7. Expression patterns of new rice miRNAs that are conserved in another monocot (*maize*) or in dicot (*Arabidopsis*) and monocot (*maize*). The tRNA and 5S rRNA bands were visualized by ethidium bromide staining of polyacrylamide gels and served as loading controls. Labelled RNA oligonucleotide was used as a size marker and the position was indicated.
Figure 9:
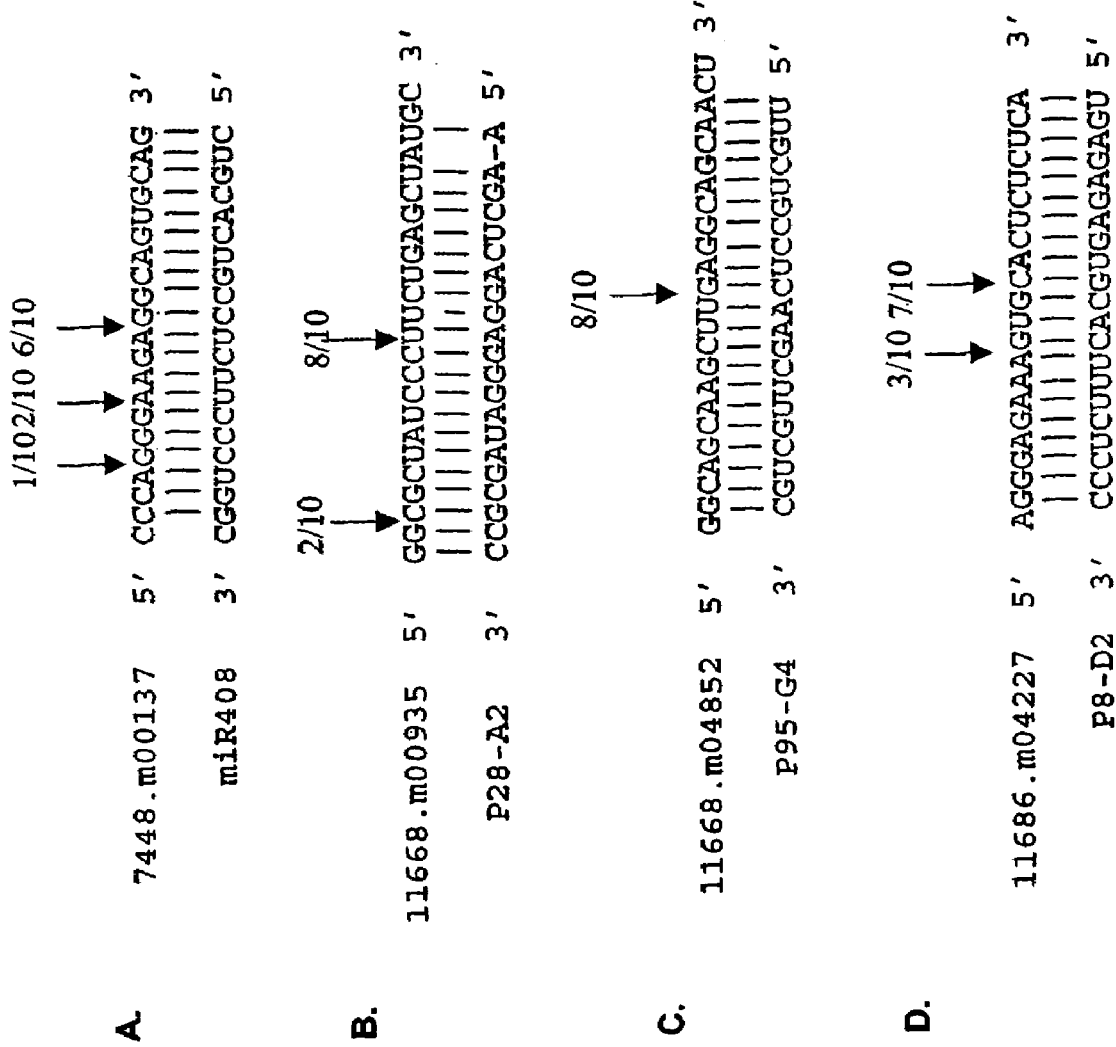
FIG. 9. Identification of miRNA-guided cleavage products of target genes in rice. (A). mRNA 7448.m00137 (SEQ ID NOS:93 and 35), (B). mRNA 11668.m00935 (SEQ ID NOS: 94 and 95), (C). mRNA 11668.m04852 (SEQ ID NOS:96 and 97) and (D). mRNA 11686.m04227 (SEQ ID NOS:98 and 99). Mapping of cleavage sites was done by RLM-5'RACE. Partial mRNA sequences from target genes were aligned with miRNAs. Numbers indicate the fraction of cloned PCR products terminating at different positions.

The tissue- and development-specific expression of miR-NAs might provide clues about their physiological function. In a wide range of organisms, many miRNAs have been found differentially expressed at different developmental stages, cell types and tissues (Lee, R. C. et al., *Science* 294:862-864 (2001); Lagos-Quintana, M. et al., *Curr. Biol.* 12:735-739 (2002); Aravin, A. et al., *Dev. Cell* 5:337-350 (2003); Houbaviy, H. B. et al., *Dev. Cell* 5:351-358 (2003)). Several *Arabidopsis* miRNAs are expressed ubiquitously while the expression of many others are regulated by development and shows preferential accumulation in certain tissues (Reinhart, B. J. et al., *Genes Dev.* 16:1616-1626 (2002); Llave, C. et al., *Plant Cell* 14:1605-1619 (2002a); Park, W. et al., *Curr. Biol.* 12:1484-1495 (2002); Sunkar, R. et al., *Plant Cell* 16:2001-2019 (2004); Jones-Rhoades, M. J. et al., *Mol. Cell* 14:787-799 (2004)). To assist with the determination of the function of the new rice miRNAs, we examined their expression in different organs and developmental stages (FIGS. 6 and 7).

The expression patterns of miR441 and miR442 are similar: moderate expression in leaves, roots and young seedlings, and weaker expression in stems and inflorescences (FIGS. 6A and 6B). miR435 and miR437 also displayed similar expression patterns: moderate expression in leaves and young seedlings and weaker expression in other tissues tested (FIGS. 6C and 6D). miR443 and miR446 seem to be strongly expressed in leaves and roots and moderately in stem and inflorescence tissues (FIGS. 6E and 6F). miR436 is expressed in all tissues tested but the levels are higher in inflorescence and young seedlings (FIG. 6G). miR438 expression was moderate in leaves, root, inflorescence and young seedlings (FIG. 6H). miR440 is uniformly and abundantly expressed in all rice tissues (FIG. 6I), while miR439 shows very weak expression in seedlings and is barely detectable in other tissues (FIG. 6J).

OsmiR396d showed strong and ubiquitous expression in all tissues, although the expression in roots was relatively lower (FIG. 7A). miR445 was strongly expressed in mature stems but barely detected in leaf and inflorescence tissues (FIG. 7B). OsmiR444 showed uniform expression in all rice tissues examined (FIG. 7C). All these three miRNAs (miR396d, miR444 and miR445) were found to be expressed in maize, although the signal was weaker, possibly due to pooled RNA from different tissues of maize (FIGS. 7A, 7B and 7C).

Some miRNAs displayed tissue- or developmental stage-specific expression patterns. Particularly interesting expression was observed for miR445 and miR390, which showed preferential expression in stems and roots, respectively (FIGS. 7B and 7D).

To help determine whether a miRNA is conserved within monocots, its expression was analyzed in another monocot, maize. The analysis showed that 3 miRNAs (miR396d, miR444 and miR445) are conserved and expressed in maize (FIGS. 7A, 7B and 7C). The presence of miR396d and miR445 miRNAs in other monocots is supported by their expression in maize, and miR444 by sequence and expression. In addition, miR437 sequence and conserved precursor fold-back structures are present in maize, sugarcane and *Sorghum* (FIG. 12). The absence of sequence and expression of these 4 miRNAs in *Arabidopsis* suggests that they may be specific to monocots. As an example of conserved miRNAs between dicots and monocots, we tested the expression of a newly identified and conserved miRNA, miR390, in addition to the previously reported and conserved OsmiR156 and OsmiR171 miRNAs in rice, maize and *Arabidopsis* (FIGS. 7D, 7E and 7F). In addition to the expected size, the OsmiR171 probe also hybridized to a slightly larger (~23 bp) small RNA species in maize but not in rice or *Arabidopsis*, indicating that this larger species is specific to maize (FIG. 7E). The remaining 9 new rice miRNAs appear not conserved between plant species since they have no counterparts in other known plant sequences and their expression could not be detected in maize or *Arabidopsis*.

In summary, the Northern blot analysis confirmed the expression and sizes of 14 newly identified miRNAs in rice (FIGS. 6 and 7). The majority is expressed ubiquitously in all tissues.

Predicted Targets

Prediction of plant miRNA targets has been facilitated by their extensive sequence complementarity (Rhoades, M. et al., *Cell* 110:513-520 (2002); Jones-Rhoades, M. J. et al., *Mol. Cell* 14:787-799 (2004); Sunkar, R. et al., *Plant Cell* 16:2001-2019 (2004); Bonnet, E. et al., *Proc. Natl. Acad. Sci. USA.* 101:11511-11516 (2004); Wang, X. J. et al., *Genome Biol.* 5:R65 (2004b); Adai, A. et al., *Genome Res.* 15:78-91 (2005)). Regulatory targets can be more confidently predicted for conserved miRNAs, because complementary sites often are conserved across species boundaries. To identify the potential targets of our newly identified miRNAs, we used the miRNA sequences to search the rice mRNA sequences for antisense hits with the PATSCAN program (Dsouza, M. et al., *Trends Genet.* 13:497-498 (1997)). Based on transcriptome analysis in *Arabidopsis* transgenic plants over-expressing miRNAs, Weigel and colleagues (Schwab, R. et al., *Dev. Cell* (in press) (2005)) devised a set of rules for predicting miRNA targets. These criteria include, allowing one mismatch in the region complementary to nucleotides 2-12 of the miRNA but not at the cleaving site (10 and 11 nt), and 3 additional mismatches were permitted between 12 and 21 nt positions, but no more than 2 continuous mismatches within this region. Adopting these rules in predicting newly identified miRNA targets in rice, we allowed 1 mismatch between the positions 1-9 nt from the 5' end of miRNA, no mismatches between positions 10 and 11, another two mismatches were allowed between positions 12 and 21/24. Gaps and mismatches are commonly seen in known animal and plant miRNA::mRNA base-pairing interactions that are known to lead to cleavage or attenuation of translation (Palatnik, J. F. et al., *Nature* 425:257-263 (2003); Aukerman, M. J. et al., *Plant Cell* 15:2730-2741 (2003); Chen, X. *Science* 303:2022-2025 (2004); Jones-Rhoades, M. J. et al., *Mol. Cell* 14:787-799 (2004)). By applying the above rules, our analysis led to the prediction of 46 genes as putative targets for 11 new miRNAs in rice (Table 3). Predicted targets and their complementarity with the new miRNAs are provided in Table 4. The number of predicted targets per miRNA varied greatly, from 1 to 15. Four of the miRNAs (miR435, miR443, miR444 and miR445) each has only one predicted target. We were unable to predict targets for the remaining 3 miRNAs (miR438, miR440 and miR442) by applying these criteria. To evaluate the false positive rates of our target predictions, we performed the same searches with 100 randomized sequences for each miRNA. The length and composition of the miRNAs was maintained in the randomized sets and the searches were performed with the same mismatch settings (Rhoades, M. et al., *Cell* 110:513-520 (2002); Jones-Rhoades, M. J. et al., *Mol. Cell* 14:787-799 (2004)). According to these results (Table 3) the hit frequency with the authentic miRNAs is in most cases more than 5 times higher and relative.

In animals, all known miRNA target sites were found in 3'UTR's of protein coding genes, whereas in plants they are only occasionally in the 3'UTRs and but are predominantly in the coding regions (Rhoades, M. et al., *Cell* 110:513-520 (2002); Jones-Rhoades, M. J. et al., *Mol. Cell* 14:787-799 (2004); Sunkar, R. et al., *Plant Cell* 16:2001-2019 (2004); Bonnet, E. et al., *Proc. Natl. Acad. Sci. USA.* 101:11511-11516 (2004); Wang, X. J. et al., *Genome Biol.* 5:R65 (2004b); Adai, A. et al., *Genome Res.* 15:78-91 (2005)). In plants, they also have been predicted to reside in 5'UTRs (Sunkar, R. et al., *Plant Cell* 16:2001-2019 (2004)). Recently, miRNAs have also been predicted to target ORFs in humans (Lewis, B. P. et al., *Cell,* 120:15-20 (2005)). Consistent with the earlier findings in *Arabidopsis,* 30 of our predicted target genes in rice have target sites in their ORFs. Fifteen genes have their predicted target sites in 3' UTR and only one in the 5' UTR.

Both miR444 and its predicted target, a MADS-box transcription factor gene, are conserved in other monocots such as wheat, maize, barley and sugarcane but not in *Arabidopsis* (data not shown). OsmiR396d, a new member of the miR396 family, is expected to target the GRFs (Jones-Rhoades, M. J. et al., *Mol. Cell* 14:787-799 (2004)). miR396d displays near perfect complementarity with 15 of these GRF genes (Table 3 and Table 4). The complementary sites of miR396d are highly conserved in GRF genes of sorghum, maize, barley and sugarcane.

The predicted target of miR439, 11667.m02576, a dirigent-like protein gene, was found to have 3 complementary sites within its ORF (FIG. 8). These 3 sites are very closely spaced and separated by gaps of 11 and 9 nt. One target site corresponding to the positions 567-588 is perfectly complementary to the miRNA. The other two target sites correspond to the positions 599-619 and 628-648, with 2 and 4 mismatches, respectively (FIG. 8). The two target sites corresponding to positions 567-588 and 628-648 are in frame and there is partial amino acid sequence conservation between these two target sites (FIG. 8). The presence of 3 target sites within one ORF has not been seen before and thus is unique among miRNA targets predicted thus far.

It appears that our predicted targets have roles not only in development but also in diverse physiological processes. Sixteen of the predicted targets of 2 miRNAs (miR396d and miR444) are transcription factors (GRL transcription factors and MADS-box transcription factor), whereas the remaining 30 predicted targets of 9 miRNAs appear to have roles in a broad range of physiological processes, and include protein kinases, F-box proteins, dirigent-like protein, glutamate receptor-like proteins, RNA binding protein, retrotransposon and 17 other proteins with unknown function (Table 3).

Identification of miRNA-Guided Cleavage of Target mRNAs in Rice miRNAs negatively regulate target genes, through miRNA-directed cleavage within the region of complementarity or interfering with translation (Carrington, J. C. et al. *Science* 301:336-338 (2003); Bartel, D. P. *Cell* 116:281-297 (2004); Ambros, V. *Nature* 431:350-355 (2004); Dugas, D. V. et al., *Curr. Opin. Plant Biol.* 7:512-520 (2004); Mallory, A. C. et al., *Curr. Opin. Plant Biol.* 7:120-125 (2004a)). Most of the *Arabidopsis* miRNAs have been shown to guide the cleavage of target mRNAs (Llave, C. et al., *Science* 297:2053-2056 (2002b); Tang, G. et al., *Genes Dev.* 17:49-63 (2003); Palatnik, J. F. et al., *Nature* 425:257-263 (2003); Kasschau, K. et al., *Dev. Cell* 4:205-217 (2003); Xie, Z. et al., *Curr. Biol.* 13:784-789 (2003); Mallory, A. C. et al., *Curr. Biol.* 14:1035-1046 (2004b); Mallory, A. C. et al., *EMBO J.* 23:3356-3364 (2004c); Floyd, S. K. et al., *Nature* 428:485-486 (2004); Jones-Rhoades, M. J. et al., *Mol. Cell* 14:787-799 (2004); Wang, X. J. et al., *Genome Biol.* 5:R65 (2004b)). To test whether the predicted miRNA targets in rice can also be cleaved, we used a RNA ligase-mediated 5' RACE procedure (Llave, C. et al., *Science* 297:2053-2056 (2002b)) to map the cleavage sites in the predicted target genes from rice. We performed the 5'RACE assays on four predicted target genes: two were representatives of targets of conserved miRNAs (11668.m00935 targeted by OsmiR390; 7448.m00137 targeted by OsmiR408); one is a MADS-box factor (11668.m04852) which is a predicted target of OsmiR444 as a representative of monocot-specific miRNA target; and the other target served as a representative of rice specific miRNA target (11686.m04227 targeted by OsmiR436). All these four predicted targets were found to have specific cleavage sites corresponding to the miRNA complementary sequences (FIGS. 9A, 9B, 9C and 9D). In all these cases, the most common 5' end of the mRNA fragments mapped to the nucleotides that pair with the 10th miRNA nucleotides from their 5' ends.

Experimental Verification of Previously Predicted miRNAs in Rice

With the exception of a member of the miR171 family, none of the predicted miRNAs in rice have been verified experimentally. The miR171b homolog in rice has been cloned in a recent study (Wang, J-F. et al., *Nucleic Acids Res.* 32:1688-1695 (2004a)). Sequence similarity searches show that 21 of the cloned miRNAs (in 15 families) in this study had been predicted in rice (Table 2). These include OsmiR156a, OsmiR156k, OsmiR159a/b, OsmiR159c, OsmiR160, OsmiR164, OsmiR166a-f, OsmiR167a-c, OsmiR167d-I, OsmiR168a, OsmiR169b/c, OsmiR169f/g, OsmiR169h-m, OsmiR171a-f, OsmiR171g, OsmiR172a, OsmiR393, OsmiR397, OsmiR398, OsmiR399a and OsmiR408 (Table 2). We noticed that all predicted members of 4 miRNA families—OsmiR169 (3 members), OsmiR156 (2 members), OsmiR159 (2 members) and OsmiRl71 (2 members)—have appeared in our libraries (Table 2). Thus, our cloning supports the expression of all members of these 4 miRNA families in rice.

The frequency of cloning varies highly among miRNAs. Our analysis indicates that OsmiR168a is the most abundant miRNA in rice, which was represented by 22 clones in the library. Of the 22 clones, 14, 5 and 3 came from shoot, root and inflorescence libraries, respectively. The OsmiR168 family was represented by 2 members (168a and 168b) that differ slightly in nucleotide sequence. All 22 clones belong to OsmiR168a and none to miR168b, which suggests that only miR168a is abundantly expressed, and miR168b is much lower in abundance or its expression may be limited to specific cells or tissues. An equally abundant miRNA family is the OsmiR156 family, with multiple (12) loci in the rice genome, which appeared 22 times in our sequencing. Seventeen clones corresponded to the OsmiR156a-j loci, whereas the other 5 clones belong to another homolog, miR156k/l. Slightly less abundant miRNAs are members of the OsmiR396 and OsmiR169 families, each represented by 10 and 9 clones, respectively. Interestingly, none of the 10 clones represented the predicted member of the OsmiR396 family; rather, all these 10 clones corresponded to the new member, OsmiR396d, identified in this study. Other miRNAs, OsmiR159, OsmiR164, OsmiR166, OsmiR167, OsmiR169, OsmiR171, OsmiR172 and OsmiR397, were cloned only a few times (2 to 8), whereas the rest (OsmiR160, OsmiR393, OsmiR398, OsmiR399 and OsmiR408) appeared only once.

In addition to the 14 new miRNAs presented in the Table 1, we also identified 5 other small RNAs (Table 5) encoded by the rice genome and have some features of miRNAs (derived from hairpin RNA precursors) (FIG. 13). However, we are unable to designate them as miRNAs at the present time as they could not be detected in the Northern analysis. Due to the lack of genetic tools in rice for validating miRNA biogenesis, such as mutants defective in DCL genes, future research is required to confidently designate these small RNAs as either miRNAs or siRNAs.

DISCUSSION

Monocot-specific and Rice-specific miRNAs

In animals, most miRNAs are conserved across species boundaries (Ambros, V. *Nature* 431:350-355 (2004); Bartel, D. P. *Cell* 116:281-297 (2004)). The strict conservation of miRNAs observed might suggest that the interactions between these miRNAs and their targets constitute essential processes and could play evolutionarily conserved roles (Pasquinelli, A. E. et al., *Nature.* 408:86-89 (2000)). However, a few miRNAs appear to be species specific (Ambros, V. et al., *Curr. Biol.* 13:807-818 (2003a)). miRNAs that are restricted to one or a few species may be implicated in species- or clade-specific functions. The identification of several miRNAs in *Arabidopsis* that are not conserved in rice suggests that these may have specific roles in *Arabidopsis*. These observations strongly supported the hypothesis that rice may also have a unique set of miRNAs. Thus far, 20 families of miRNAs discovered in *Arabidopsis* are predicted to be conserved in rice (Reinhart, B. J. et al., *Genes Dev.* 16:1616-1626 (2002); Park, W. et al., *Curr. Biol.* 12:1484-1495 (2002); Jones-Rhoades, M. J. et al., *Mol. Cell* 14:787-799 (2004); Sunkar, R. et al., *Plant Cell* 16:2001-2019 (2004); Bonnet, E. et al., *Proc. Natl. Acad. Sci. USA.* 101:11511-11516 (2004); Wang, X. J. et al., *Genome Biol.* 5:R65 (2004b); Adai, A. et al., *Genome Res.* 15:78-91 (2005)). Of these, we have experimentally verified the expression of 15 families of miRNAs in rice. To a certain extent, the 75% coverage of predicted miRNAs in our libraries may reflect the extent of saturation of our miRNA cloning. Of the 14 new rice miRNAs we identified, only 1 (miR390) is conserved in both *Arabidopsis* and maize, whereas 4 others (miR396d, miR437, miR444 and miR445) are conserved in other monocots such as maize, barley, sugarcane and *Sorghum* but not in *Arabidopsis*, which suggests that these latter ones are specific to monocots, and the remaining 9 miRNAs are likely specific to rice. All of the new miRNAs are conserved in another rice subspecies, *Indica* (Table 1). This is expected given the extensive sequence co-linearity between these two rice subspecies (Feng, Q. et al., *Nature* 420:316-320 (2002)).

Compared to computational approaches, direct cloning has the advantage of identifying not only non-conserved miRNAs, but also atypical miRNAs. Cloning of miRNAs in rice resulted in the identification of an additional member (from the OsmiR396d and OsmiR396e loci) of the OsmiR396 family. The presence of an extra nucleotide in the middle of a miRNA from the same family was previously unknown. The identification of a new member of the OsmiR396 family with the added nucleotide in the miRNA sequences suggests that future computational approaches should incorporate this structural feature in their prediction strategies. It is interesting that this new member is missing from the *Arabidopsis* miR396 family.

Unusual Processing and Ubiquitous Expression Patterns of Rice miRNAs

Although the majority of the new miRNAs are mapped to intergenic regions, a considerable fraction maps to the introns, whereas 2 miRNAs (OsmiR436 and OsmiR444) map to exons of protein-coding genes. The expression of exon- and intron-derived miRNAs in the sense polarity is most likely driven by the promoters of the surrounding genes, whereas those in the antisense polarity within the introns are likely to be expressed as independent genes.

The structural analysis of full-length transcripts of pre-miRNA transcripts of miR172 revealed the presence of introns, and the processed transcripts are 5' capped and poly-adenylated (Aukerman, M. J. et al., *Plant Cell* 15:2730-2741 (2003)). A fold-back structure can be readily predicted for the AthmiR172 precursor from genomic sequence since the hairpin precursor resides in one exon. Nevertheless, this observation suggests that certain miRNA precursor sequences can enter the spliceosomal pathway. Consistent with this, we found that one of the newly identified miRNA precursors (OsmiR444) requires part of exons 2 and 3 of a protein-coding gene for hairpin formation. This shows that some miRNA precursors undergo processing and that processed transcripts are necessary for the prediction of the hairpin structure. Similarly, a hairpin structure for miR436 could only be predicted from a processed transcript, which suggests the presence of introns within the hairpin sequence. These findings raise the possibility that some other miRNA transcripts might also have introns within the hairpin precursor sequences and it would be impossible to predict these miRNAs if the sequences of processed transcripts are not available.

Although the expression of several miRNAs from *Arabidopsis* are shown to be constitutive and ubiquitous, many miRNAs exhibit preferential expression in a temporal or tissue-specific manner (Reinhart, B. J. et al., *Genes Dev.* 16:1616-1626 (2002); Park, W. et al., *Curr. Biol.* 12:1484-1495 (2002); Llave, C. et al., *Plant Cell* 14:1605-1619 (2002a); Aukerman, M. J. et al., *Plant Cell* 15:2730-2741 (2003); Chen, X. *Science* 303:2022-2025 (2004); Sunkar, R. et al., *Plant Cell* 16:2001-2019 (2004); Jones-Rhoades, M. J. et al., *Mol. Cell* 14:787-799 (2004)), while the expression of others is modulated by abiotic stress (Sunkar, R. et al., *Plant Cell* 16:2001-2019 (2004)) or nutritional status such as sulfur starvation (Jones-Rhoades, M. J. et al., *Mol. Cell* 14:787-799 (2004)). Most of the previously reported miRNAs were shown to be abundantly expressed in inflorescence tissues in *Arabidopsis* (Reinhart, B. J. et al., *Genes Dev.* 16:1616-1626 (2002); Llave, C. et al., *Plant Cell* 14:1605-1619 (2002a); Park, W. et al., *Curr. Biol.* 12:1484-1495 (2002); Sunkar, R. et al., *Plant Cell* 16:2001-2019 (2004)). However, the expression of most of the newly identified rice miRNAs does not show higher expression in inflorescence tissues. In fact, with the exception of OsmiR436, all others seem to have lower levels of expression in the inflorescence compared to other tissues. Additionally, most of the newly identified rice miRNAs are ubiquitously expressed and few showed tissue specific expression.

Predicted Targets Include Transcription Factors and Others with a Broad Range of Biological Functions Over one third of the genes in the human genome were predicted as miRNA targets and these targets appear to be involved in a wide range of biological functions (Lewis, B. P. et al., *Cell,* 120:15-20 (2005)). Previously reported miRNAs in *Arabidopsis* have targets that are predominantly transcription factors or parts of the RNAi machinery such as DCL-1 and AGO1 (Xie, Z. et al., *Curr. Biol.* 13:784-789 (2003); Vaucheret, H. et al., *Genes Dev.* 18:1187-1197 (2004)). More recently identified miRNAs in *Arabidopsis* may target transcripts that encode proteins involved in diverse physiological processes (Jones-Rhoades, M. J. et al., *Mol. Cell* 14:787-799 (2004); Sunkar, R. et al., *Plant Cell* 16:2001-2019 (2004); Bonnet, E. et al., *Proc. Natl. Acad. Sci. USA.* 101:11511-11516 (2004); Wang, X. J. et al., *Genome Biol.* 5:R65 (2004b); Adai, A. et al., *Genome Res.* 15:78-91 (2005)).

We were able to predict 46 genes as potential targets of 11 newly identified miRNAs in rice. Transcription factors (GRL and MADS-box gene) represented one-third of the predicted targets of miRNAs in the present study. The remaining 30 predicted targets appear to have roles in diverse physiological processes. For instance, F-box proteins that regulate diverse cellular processes, including cell cycle regulation, circadian rhythm, flower development and hormonal signal transduction (Kuroda, H. et al., *Plant Cell Physiol.* 43:1073-1085 (2002)), are predicted targets of 3 miRNAs (miR435, miR441 and miR446). OsmiR439 is predicted to target a dirigent-like protein (Table 3). Thus far, dirigent proteins and their homologs have only been reported in vascular plants (Davin, L. B. et al., *Plant Physiol.* 123:453-461 (2000)). Although the precise role of these proteins is not known, they seem to function in the lignification in vascular plants (Burlat, V. et al., *Phytochem.* 57:883-897 (2001)). Glutamate receptor proteins are probable targets of OsmiR437 (Table 3). Ionotropic glutamate receptors function in animals as glutamate-gated non-selective cation channels. Recent evidence suggests that plant glutamate-receptor-like (GLR) genes do encode non-selective cation channels, but these channels are not gated by amino acids and therefore their roles in plants remain a mystery (Davenport, R., *Ann. Bot.* 90:549-557 (2002)). OsmiR390 is predicted to target 3 leucine rich-repeat protein kinases (Table 3). Fifteen unknown proteins are also predicted targets of newly identified miRNAs (Table 3). The identification of miRNAs that target genes with unknown functions provides a unique tool to probe the functions of these unknown genes.

The MADS-box protein family is represented by >70 and >100 genes in rice and *Arabidopsis*, respectively. No miRNA that targets the MADS-box transcription factors has been identified previously, either in *Arabidopsis* or rice. In this study, we found a miRNA (miR444) that targets a MADS-box transcription factor gene in rice, and both the miRNA and the target sites in the MADS-box genes are conserved in monocots. MADS-domain proteins in plants were first identified as regulators of floral organ identity and have since been found to control additional developmental processes such as meristem identity, root development, fruit dehiscence, and flowering time (Coen, E. S. et al., *Nature* 353:31-37 (1991); Weigel, D. et al., *Cell* 78:203-209 (1994); Riechmann, J. L. et al., *Biol. Chem.* 378:1079-1101 (1997); Theissen, G. et al., *Plant Mol. Biol.* 42:115-149 (2000)). miR444 precursors can be found in other monocot species such as maize, wheat, barley, and sugarcane from expression databases. The lack of a miR444 homolog and of the conserved target site in a MADS-box gene(s) from *Arabidopsis* strongly suggests that this miRNA-mediated regulation of MADS-box genes is conserved only in monocots. Future manipulation of OsmiR444 level and of the target MADS-box genes should help unravel the importance of these interactions in rice and in monocots in general.

To our knowledge, no plant or animal miRNA has been previously predicted to have multiple target sites in one ORF. In the case of OsmiR439, one target site is perfectly complementary and the other two target sites have 2 and 4 mismatches including in positions 9 and 11 from the 5' end of the miRNA. The mismatch at position 11 may suggest that the interaction does not lead to cleavage, since perfect match at positions 10 and 11 are important for cleavage of the target (Jones-Rhoades, M. J. et al., *Mol. Cell* 14:787-799 (2004); Schwab, R. et al., *Dev. Cell* (in press) (2005)). However, more recently it is shown that a mismatch at position 11 reduces the cleavage rate but still can be tolerated in vivo (Mallory, A. C. et al., *EMBO J.* 23:3356-3364 (2004c)). The identification of miR439, with 3 complementary target sites within the ORF of a target gene (FIG. 8), suggests that the cooperative regulation of 1 gene at 3 different sites by 1 miRNA may be important to downregulate the mRNA to the required level. Alternatively, despite its perfect complementarity with the target gene at one of the target sites, this miRNA might be involved in translational repression for which more than 1 target site may be necessary. Or, 1 target site may be involved in cleavage and the others may be important for translational repression. Future functional studies with introduced silent mutations in the target sites may reveal the importance of 3 target sites in 1 ORF and may shed light on potentially unique regulatory mechanisms.

miRNA-guided Cleavage of Target mRNAs in Rice

The cleavage of target mRNAs appears to be the predominant mode of gene regulation by plant miRNAs (Llave, C. et al., *Science* 297:2053-2056 (2002b); Kasschau, K. et al., *Dev. Cell* 4:205-217 (2003); Palatnik, J. F. et al., *Nature* 425:257-263 (2003); Tang, G. et al., *Genes Dev.* 17:49-63 (2003); Xie, Z. et al., *Curr. Biol.* 13:784-789 (2003); Jones-Rhoades, M. J. et al., *Mol. Cell* 14:787-799 (2004); Vaucheret, H. et al., *Genes Dev.* 18:1187-1197 (2004); Mallory, A. C. et al., *Curr. Biol.* 14:1035-1046 (2004b); Mallory, A. C. et al., *EMBO J.* 23:3356-3364 (2004c)). Target mRNA fragments resulting from miRNA-guided cleavage are characterized by a 5' phosphate group, and cleavage occurs near the middle of the base-pairing interaction region with the miRNA (Llave, C. et al., *Science* 297:2053-2056 (2002b)). We were able to map the cleavage sites for 4 of the predicted targets, and the results support that these are genuine miRNA targets in rice.

OsmiR408 was cloned in this study (Table 2). Previously, we reported the identification of miR408 from *Arabidopsis* (Sunkar, R. et al., *Plant Cell* 16:2001-2019 (2004)). miR408 was predicted to target an mRNA encoding a plantacyanin (7448.m00137). Its target site is conserved in several plant species (Sunkar, R. et al., *Plant Cell* 16:2001-2019 (2004)). In the present study, we mapped the miR408 cleavage site in the rice plantacyanin transcript by using a modified 5' RACE procedure. The result validated plantacyanin as a genuine target of OsmiR408. The precise function of plantacyanins in plants is unknown; however, they have been proposed to function in cell-to-cell signaling, lignin formation and stress responses (Romo, S. et al., Plant Physiol. Biochem. 39:1017-1026 (2001); Kim, S. et al., *Proc. Natl. Acad Sci. USA*, 100: 16125-16130 (2003)). Our ability to map the cleavage products that correspond to the OsmiR390 complementary site in a Ser/Thr/Tyr-protein kinase (11668.m00935) confirms that this kinase is indeed a miRNA target. This is the first demonstration that protein kinases can be targeted by miRNAs. We also provide evidence that a rice MADS-box transcription factor (11668.m04852) is a genuine target of OsmiR444. One of the predicted targets (11686.m04227 an unknown protein) of miR436 is also confirmed by the cleavage analysis.

In summary, our cloning study led to the discovery of 14 new rice miRNAs, of which only one (miR390) is conserved in *Arabidopsis*. At least four of the miRNAs (miR396d, miR437, miR444 and miR445) appear to be limited to monocots, suggesting monocot-specific miRNA-dependent regulatory processes. It is possible that more of the new miRNAs are present in other monocots whose sequence information is not available. It is also possible that more of these miRNAs may be conserved in maize but cannot be detected with the rice specific probes because of possible subtle sequence differences. The putative monocot-specific miRNAs may have evolved after the divergence of monocots and dicots 200 million years ago, or they may have been lost in dicots.

METHODS

Cloning of miRNAs from Rice

Total RNA was isolated separately from shoots and roots of 4-week-old young seedlings and inflorescence of adult rice (*Oryza sativa* spp *japonica* cv. Nipponbare) plants using TRIzol (Bethesda Research laboratories, Life technologies) according to the manufacturer's instructions. Cloning of miRNAs was performed as described (Sunkar, R. et al., *Plant Cell* 16:2001-2019 (2004)). In brief, small RNAs from 18 to 26 nt were size fractionated, purified, and ligated sequentially to 5' and 3' RNA/DNA chimeric oligonucleotide adapters.

Reverse transcription was performed after ligation with the adapters, followed by PCR amplification. The resulting PCR products were cloned and transformed into competent cells. Plasmids were isolated from individual colonies and sequenced. The sequences were subsequently processed and used for BLAST analysis against the *Oryza sativa* spp *japonica* sequences in the TIGR database and other plant sequences in the NCBI database.

Sequence Analysis and Prediction of Fold-back Structures

Automated base calling of raw sequence traces and vector removal was performed with the PHRED and CROSS MATCH programs from Ewing and Green (1998). All trimmed sequences longer than 16 nt were used to search the Rfam (web site is sanger.ac.uk/Software/Rfam) database with BLASTN (Altschul, S. F. et al., *Nucleic Acids Res.* 25:3389-3402 (1997)). This step allowed the removal of most non-siRNA and non-miRNA species in the dataset. Putative origins for the remaining sequences were identified by BLASTN searches against the intergenic and intron sequences using the latest annotation 3.0 of *Oryza sativa* spp. *japonica* from The Institute for Genomic Research (TIGR, web site is ftp.tigr.org/pub/data/Eukaryotic _Projects/o_sativa/). Candidates with perfect matches against these genomic datasets were used for fold-back secondary structure prediction with the mfold program (Zuker, M. *Nucleic Acids Res.* 31:3406-3415 (2003)). Three different combinations of upstream and downstream sequence spanning the putative miRNA origins were used for the predictions: (1) 400 bp upstream and 20-30 bp downstream (2) the same length combination but in reverse order and (3) 200 bp upstream and 200 bp downstream. In the case of OsmiR444 and OsmiR436, only processed transcript sequences were used to predict the hairpin structure. OsmiR436 hairpin prediction required 700 nt.

To identify putative target sequences, all predicted and cloned CDS and UTR sequences from *O. sativa* (TIGR all.cdna set) were searched with PatScan (Dsouza, M. et al., *Trends Genet.* 13:497-498 (1997)). The following parameters were used for these pattern searches, all referring to the 5' end of the miRNAs in antisense orientation: not more than one mismatch between positions 1-9, no mismatch between positions 10-11 and not more than two mismatches for the rest of the sequence. False positive rates of predicted targets were estimated with the same search strategy using 100 randomized samples for each miRNA. The retrieved miRNA/target site pairs were ranked and scored by aligning them with the Needleman-Wunsch global alignment program from EMBOSS (Rice, P. et al., *Trends Genet.* 16:276-277 (2000)).

Global cross-species conservations of miRNAs were determined by BLASTN searches against the NT and EST databases from NCBI. The results were parsed with a Perl script that scored only those pairwise BLAST alignments (HSP) as hits when they were not more than two positions shorter than the query sequence and 95% identical. More detailed conservations of miRNAs and target sequences within the genome sequences of *Populus trichocarpa, O. sativa* spp. *indica* and *Arabidopsis thaliana* were determined with the same BLASTN and PatScan strategy used for the japonica host. Weaker conserved origins in the genomic sequences of *Arabidopsis* and *Populus trichocarpa* were identified with PatScan (maximal two mismatches) and subsequent fold-back structure predictions.

RNA Blot Analysis

Total RNA was isolated from leaf, stem, root and inflorescence tissues of adult plants as well as from 4-week-old young rice seedlings. Total RNA was also isolated from pooled maize tissues (kernels, pericarp, endosperm, scutellum, coleoptile, embryo, silk and young seedlings) and 3-week-old *Arabidopsis* seedlings using TRIzol (Bethesda Research laboratories, Life technologies). One hundred micrograms of total RNA was loaded per lane and resolved on a denaturing 15% polyacrylamide gel and transferred electrophoretically to Hybond-N$^+$ membranes (Amersham Biosciences, Bucks, UK). Hybridization and washings were performed as described (Sunkar, R. et al., *Plant Cell* 16:2001-2019 (2004)). The membranes were briefly air dried and then exposed to a phosphorimager.

5' RACE

Total RNA from 4-week-old rice seedlings was extracted with Trizol reagent. Poly(A)$^+$ mRNA was purified from total RNA with use of the Poly A kit (Promega). RLM-5' RACE (RNA ligase mediated-5' rapid amplification of cDNA ends) was carried out with use of the GeneRacer Kit (Invitrogen Life Technologies, Carlsbad, Calif., USA). The GeneRacer RNA Oligo adapter was directly ligated to mRNA (100 ng) without calf intestinal phosphatase and tobacco acid pyrophosphatase treatment. Gene specific primers were designed and used for cDNA synthesis. Initial PCR was carried out with the GeneRacer 5' primer and gene specific primers (7448.m00137, 11668.m00935, 11668.m04852 and 11686.m04227). Nested PCR was carried out with 1 µL of the initial PCR reaction, GeneRace 5' nested primer, and gene specific internal primers. After amplification, 5' RACE products were gel-purified and cloned, and at least 10 independent clones were sequenced.

TABLE 1

New rice miRNAs identified by cloning.

| miRNA | Sequence (5' → 3') (SEQ ID NOS: 1-14) | RNA blot | size (nt) | No. of loci | Chr. | Fold-Back (5'/3') | intergenic/intron/exon | Osi | Zm | At | Pt |
|---|---|---|---|---|---|---|---|---|---|---|---|
| miR390 | AAGCUCAGGAGGGAUAGCGCC (2) | + | 21 | 1 | 3 | 5' | intergenic | + | + | + | + |
| miR396d | UCCACAGGCUUUCUUGAACUG (10) | + | 21 | 2 | 4 | 5' | intergenic | + | + | − | − |
| miR396e | | | | | 2 | 5' | intergenic | | | | |
| miR435 | UUAUCCGGUAUUGGAGUUGA (2) | + | 20 | 1 | 3 | 3' | 11669.m03227_Intron_7(s) | + | − | − | − |
| miR436 | UGAGAGAGUGCACUUCUCCC (2) | + | 21 | 1 | 2 | 5' | J023035E19 | + | − | − | − |
| miR437 | AAAGUUAGAGAAGUUUGACUU (2) | + | 21 | 1 | 2 | 3' | 11668.m02729_Intron_15(s) | + | + | − | − |
| miR438 | UUCCCACGCGUUAUAGUGAAA (1) | + | 21 | 1 | 6 | 5' | intergenic | + | − | − | − |
| miR439a | UGUCGAACCGCG GUUGUUCGA (1) | + | 21 | 10 | 1 | 3' | intergenic | + | − | − | − |
| miR439b | | | | | 10 | 3' | intergenic | | | | |
| miR439c | | | | | 1 | 3' | intergenic | | | | |

TABLE 1-continued

New rice miRNAs identified by cloning.

| miRNA | Sequence (5' → 3') (SEQ ID NOS: 1-14) | RNA blot | size (nt) | No. of loci | Chr. | Fold-Back (5'/3') | intergenic/intron/exon | Osi | Zm | At | Pt |
|---|---|---|---|---|---|---|---|---|---|---|---|
| miR439d | | | | | 3 | 3' | intergenic | | | | |
| miR439e | | | | | 7 | 3' | intergenic | | | | |
| miR439f | | | | | 8 | 3' | intergenic | | | | |
| miR439g | | | | | 8 | 3' | intergenic | | | | |
| miR439h | | | | | 6 | 3' | intergenic | | | | |
| miR439i | | | | | 9 | 3' | intergenic | | | | |
| miR439j | | | | | 10 | 3' | 11676.m02626__Intron_1(s) | | | | |
| miR440 | AGUGUCUCCUGAUGAUCGGGACAA (2) | + | 24 | 1 | 11 | 3' | 11687.m01522__Intron_9(s) | + | – | – | – |
| miR441a | UACCAUCAAUAUAAAUGUGGGAAA (3) | + | 24 | 3 | 1 | 3' | intergenic | + | – | – | – |
| miR441b | | | | | 3 | 3' | intergenic | | | | |
| miR441c | | | | | 7 | 3' | intergenic | | | | |
| miR442 | UGACGUGUAAAUUGCGAGACGAAU (2) | + | 24 | 1 | 4 | 5' | 11670.m05347__Intron_1(s) | + | – | – | – |
| miR443 | AUCACAAUACAAUAAAUCUGGA (2) | + | 22 | 1 | 3 | 5' | intergenic | + | – | – | – |
| miR444 | UUGCUGCCUCAAGCUUGCUGC (3) | + | 21 | 1 | 8 | 3' | J033125N22(s) | + | + | – | – |
| miR445a | UAAAUUAGUGUAUAAACAUCCGAU (2) | + | 24 | 9 | 5 | 3' | intergenic | + | + | – | – |
| miR445b | | | | | 6 | 3' | intergenic | | | | |
| miR445c | | | | | 12 | 3' | intergenic | | | | |
| miR445d | | | | | 3 | 3' | intergenic | | | | |
| miR445e | | | | | 7 | 3' | intergenic | | | | |
| miR445f | | | | | 3 | 3' | intergenic | | | | |
| miR445g | | | | | 6 | 3' | intergenic | | | | |
| miR445h | | | | | 3 | 3' | 11669.m00786__Intron_2(as) | | | | |
| miR445i | | | | | 6 | 3' | 11680.m00766__Intron_1(s) | | | | |
| miR446 | CAUCAAUAUGAAUAUGGGAAAUGG (2) | + | 24 | 1 | 6 | 3' | intergenic | + | – | – | – |

Frequency of cloning is indicated in parentheses after the miRNA sequences. Chromosomal (Chr.) position is indicated. miRNA location in the predicted fold-back structure is specified (5' or 3' arm). miRNAs that are conserved in other plants are indicated. Osi: *Oryza sativa* subspecies *indica*; Zm: *Zea mays*; At: *Arabidopsis thaliana*; Pt: *Populus trichocarpa*

TABLE 2

Experimental verification of previously predicted miRNAs in rice.

| Gene | miRNA sequence (SEQ ID NOS: 15-35) | Cloning frequencies in libraries |
|---|---|---|
| OsmiR156a-j | UGACAGAAGAGAGUGAGCAC | Shoot (12), Root (5) |
| OsmiR156k,1 | UGACAGAAGAGAGUGAGCACA | Shoot (3), Root (1), Inflorescence (1) |
| OsmiR159a,b | UUUGGAUUGAAGGGAGCUCU | Shoot (3), Inflorescence (2) |
| OsmiR159c | UUGGAUUGAAGGGAGCUCUGC | Shoot (2) |
| OsmiR160 | UGCCUGGCUCCCUGUAUGCCA | Shoot (1) |
| OsmiR164 | AUGGAGAAGCAGGGCAGGUGCA | Shoot (3), Inflorescence (3) |
| OsmiR166a-f | UCGGACCAGGCUUCAUUCCCC | Shoot (2), Inflorescence (1) |
| OsmiR167a,b,c | UGAAGCUGCCAGCAUGAUCUA | Shoot (2) |
| OsmiR167d-i | UGAAGCUGCCAGCAUGAUCUG | Root (1) |
| OsmiR168a | UCGCUUGGUGGAGAUCGGGAC | Shoot (14), Root (3), Inflorescence (5) |
| OsmiR169b,c | CAGCCAAGGAUGACUUGCCGG | Shoot (2) |
| OsmiR169f,g | UAGCCAAGGAUGACUUGCCUA | Shoot (2), Root (1) |
| OsrniRl69h-m | UAGCCAAGGAUGACUUGCCUG | Shoot (1) |
| OsmiR171a-f | UGAUUGAGCCGUGCCAAUAUC | Shoot (1), Root (1), Inflorescence (2) |
| OsmiR171g | GAGGUGAGCCGUGCCAAUAUC | Root (1) |
| OsmiR172a | AGAAUCUUGAUGAUGCUGCAU | Shoot (2), Inflorescence (2) |
| OsmiR393 | UCCAAAGGGAUCGCAUUGAUC | Inflorescence (1) |
| OsmiR397b | UUAUUGAGUGCAGCGUUGAUG | Shoot (1), Root (1) |
| OsmiR398 | UGUGUUCUCAGGUCGCCCUG | Shoot (1) |
| OsmiR399a | UGCCAAAGGAGAAUUGCCCUG | Shoot (1) |
| OsmiR408 | CUGCACUGCCUCUUCCCUGGC | Root (1) |

TABLE 3

Predicted targets of newly identified rice miRNAs. For each potential target gene, the number of mismatches between the miRNA and mRNA is indicated in parentheses. Annotated rice mRNAs were also searched for sites complementary to randomized miRNAs (100 repeats) applying the same criteria that were used for predicting targets. The mean of the hit frequency of the randomized data and their standard deviations are recorded.

| miRNA | Target gene | Target site | Target protein | Count | Mean | SD |
|---|---|---|---|---|---|---|
| MIR390 | 11668.m00935(1); 11674.m03433(3); 11687.m03320(3) | ORF | LRR proteins | 3 | 0.24 | 0.7 |
| MIR396d | 11668.m04403(1); 11668.m04580(1); 11669.m04718(1); 11670.m04997(1); 11670.m04998(1); 11680.m00165(1); 11680.m00999(1); 11669.m05248(1); 11670.m02258(1); 11687.m03206(1); 11686.m02909(1); 11687.m03206(2); 11670.m04996(1); 11680.m00166(1); 11670.m04758(1) | ORF | Growth regulating factor (GRL) transcription factors | 15 | 0.19 | 0.6 |
| MIR435 | 11687.m03448(3) | ORF | F-box protein | 1 | 0.75 | 1.3 |
| MIR436 | 11686.m04227(0); 11686.m04226(1) | ORF | unknown proteins | 2 | 0.07 | 0.3 |
| MIR437 | 11680.m04605(1); 11680.m04606(1) | ORF | Glutamate receptor proteins | 2 | 0.22 | 0.6 |
| MIR439 | 11667.m02576 (3 target sites with 0, 2 and 4 mismatches) | ORF | Dirigent like protein | 4 | 0.15 | 0.5 |
| | 11680.m01869(1); 11668.m02918(3) | ORF | unknown proteins | | | |
| | 11673.m02474(3) | ORF | retrotransposon | | | |
| MIR441 | 11669.m05042(3) | ORF | unknown protein | 10 | 0 | 0 |
| | 11667.m06876(2); 11674.m00346(2); 11674.m00582(2); | 3'UTR | unknown proteins | | | |
| | 11680.m01945(2); 11674.m04930(3); 11687.m00089(3) | 3'UTR | unknown proteins | | | |
| | 11682.m03939(3); | 3'UTR | unknown proteins | | | |
| | 11668.m04341(2) | 3'UTR | F-box protein | | | |
| | 11686.m03687(3) | 3'UTR | UDP-glucoronosyl and UDP-glucosyltransferase | | | |
| MIR443 | 11687.m04039(3) | ORF | unknown protein | 1 | 0.13 | 0.4 |
| MIR444 | 11668.m04852(0) | ORF | MADS-box transcription factor | 1 | 0.19 | 0.6 |
| MIR445 | 11680.m05074(3) | 5'UTR | RNA-binding protein | 1 | 0 | 0 |
| MIR446 | 11668.m04341(2) | 3'UTR | F-box protein | 6 | 0.01 | 0.1 |
| | 11674.m00582(2); 11680.m01945(2); 11682.m04930(3); | 3'UTR | unknown proteins | | | |
| | 11682.m03939(3) | 3'UTR | unknown protein | | | |
| | 11680.m01730(2) | 3'UTR | unknown plant specific protein | | | |

TABLE 4

PATSCAN alignments of the new miRNAS
(SEQ ID NOS:36, 38, 40, 44, 46, 49, 52, 58, 66 and 68)
and their predicted targets in rice
(SEQ ID NOS:37, 39, 41-43, 45, 47-51, 53-57, 59-67 and 69).
miRNAs are presented as a reverse complemented form.

| miRNA | OSA_cDNA Hit | OSA_cDNA Hit2 | Description | Position | Length | Identity | Gaps | Score |
|---|---|---|---|---|---|---|---|---|
| MIR443 | 11687.m04039 | Os11g42970 | expressed protein | [771, 792] | 22 | 19/22 (86.4%) | 0/22 (0.0%) | 83 |
| MIR445 | 11680.m05074 | Os06g50890 | RNA recognition motif. (a.k.a RRM, RBD, or RNP domain), putative | [1155, 1178] | 24 | 21/24 (87.5%) | 0/24 (0.0%) | 93 |
| MIR446 | 11668.m04341 | Os02g44990 | F-box domain, putative | [1808, 1831] | 24 | 22/24 (91.7%) | 0/24 (0.0%) | 102 |
| MIR446 | 11674.m00582 | Os08g06500 | expressed protein | [4567, 4590] | 24 | 22/24 (91.7%) | 0/24 (0.0%) | 102 |
| MIR446 | 11680.m01730 | Os06g17390 | Plant protein family, putative | [2625, 2648] | 24 | 22/24 (91.7%) | 0/24 (0.0%) | 102 |
| MIR446 | 11680.m01945 | Os06g19990 | expressed protein | [558, 581] | 24 | 22/24 (91.7%) | 0/24 (0.0%) | 102 |
| MIR446 | 11682.m03939 | Os05g41190 | expressed protein | [985, 1008] | 24 | 21/24 (87.5%) | 0/24 (0.0%) | 93 |
| MIR446 | 11682.m04930 | Os05g51140 | expressed protein | [1540, 1563] | 24 | 21/24 (87.5%) | 0/24 (0.0%) | 93 |
| MIR437 | 11680.m04605 | Os06g46670 | Receptor family ligand | [3521, 3541] | 21 | 20/21 (95.2%) | 0/21 (0.0%) | 96 |

TABLE 4-continued

PATSCAN alignments of the new miRNAS
(SEQ ID NOS:36, 38, 40, 44, 46, 49, 52, 58, 66 and 68)
and their predicted targets in rice
(SEQ ID NOS:37, 39, 41-43, 45, 47-51, 53-57, 59-67 and 69).
miRNAs are presented as a reverse complemented form.

| | | | | | | | | |
|---|---|---|---|---|---|---|---|---|
| | | | binding region, putative | | | | | |
| MIR437 | 11680.m 04606 | Os06g46 670 | Receptor family ligand binding region, putative | [3772, 3792] | 21 | 20/21 (95.2%) | 0/21 (0.0%) | 96 |
| MIR390 | 11674.m 03433 | Os08g34 650 | Leucine Rich Repeat, putative | [861, 881] | 21 | 18/21 (85.7%) | 0/21 (0.0%) | 78 |
| MIR390 | 11687.m 03320 | Os11g36 340 | Leucine Rich Repeat, putative | [1033, 1053] | 21 | 18/21 (85.7%) | 0/21 (0.0%) | 78 |
| MIR439 | 11667.m 02576 | Os01g26 340 | Dirigent-like protein, putative | [568, 588] | 21 | 21/21 (100.0%) | 0/21 (0.0%) | 105 |
| MIR439 | 11680.m 01869 | Os06g19 250 | hypothetical protein | [579, 599] | 21 | 20/21 (95.2%) | 0/21 (0.0%) | 96 |
| MIR439 | 11668.m 02918 | Os02g30 670 | hypothetical protein | [407, 427] | 21 | 18/21 (85.7%) | 0/21 (0.0%) | 78 |
| MIR396d | 11668.m 04403 | Os02g45 570 | expressed protein | [507, 527] | 21 | 20/21 (95.2%) | 0/21 (0.0%) | 96 |
| MIR396d | 11668.m 04580 | Os02g47 280 | expressed protein | [570, 590] | 21 | 20/21 (95.2%) | 0/21 (0.0%) | 96 |
| MIR396d | 11668.m 05272 | Os02g53 690 | growth-regulating factor 1 | [378, 398] | 21 | 20/21 (95.2%) | 0/21 (0.0%) | 96 |
| MIR396d | 11669.m 04718 | Os03g47 140 | hypothetical protein | [653, 673] | 21 | 20/21 (95.2%) | 0/21 (0.0%) | 96 |
| MIR396d | 11670.m 04996 | Os04g51 190 | expressed protein | [535, 555] | 21 | 20/21 (95.2%) | 0/21 (0.0%) | 96 |
| MIR396d | 11670.m 04997 | Os04g51 190 | expressed protein | [535, 555] | 21 | 20/21 (95.2%) | 0/21 (0.0%) | 96 |
| MIR396d | 11670.m 04998 | Os04g51 190 | expressed protein | [535, 555] | 21 | 20/21 (95.2%) | 0/21 (0.0%) | 96 |
| MIR396d | 11680.m 00165 | Os06g02 560 | expressed protein | [605, 625] | 21 | 20/21 (95.2%) | 0/21 (0.0%) | 96 |
| MIR396d | 11680.m 00166 | Os06g02 560 | expressed protein | [605, 625] | 21 | 20/21 (95.2%) | 0/21 (0.0%) | 96 |
| MIR396d | 11680.m 00999 | Os06g10 310 | growth-regulating factor 1, putative | [282, 302] | 21 | 20/21 (95.2%) | 0/21 (0.0%) | 96 |
| MIR396d | 11669.m 05248 | Os03g51 970 | putative transcription activator | [419, 439] | 21 | 19/21 (90.5%) | 0/21 (0.0%) | 87 |
| MIR396d | 11670.m 02258 | Os04g24 190 | growth-regulating factor 1, putative | [827, 847] | 21 | 19/21 (90.5%) | 0/21 (0.0%) | 87 |
| MIR396d | 11670.m 04758 | Os04g48 510 | Similar to At3g52910 | [858, 878] | 21 | 19/21 (90.5%) | 0/21 (0.0%) | 87 |
| MIR396d | 11686.m 02909 | Os12g29 980 | expressed protein | [576, 596] | 21 | 19/22 (86.4%) | 0/21 (0.0%) | 87 |
| MIR396d | 11687.m 03206 | Os11g35 030 | growth-regulating factor, putative | [498, 518] | 22 | 19/22 (86.4%) | 2/22 (9.1%) | 81 |
| MIR441 | 11667.m 06876 | Os01g68 230 | expressed protein | [2354, 2377] | 24 | 22/24 (91.7%) | 0/24 (0.0%) | 102 |
| MIR441 | 11668.m 04341 | Os02g44 990 | F-box domain, putative | [1811, 1834] | 24 | 22/24 (91.7%) | 0/24 (0.0%) | 102 |
| MIR441 | 11674.m 00346 | Os08g04 300 | expressed protein | [2085, 2108] | 24 | 22/24 (91.7%) | 0/24 (0.0%) | 102 |
| MIR441 | 11674.m 00582 | Os08g06 500 | expressed protein | [4570, 4593] | 24 | 22/24 (91.7%) | 0/24 (0.0%) | 102 |
| MIR441 | 11680.m 01945 | Os06g19 990 | expressed protein | [561, 584] | 24 | 22/24 (91.7%) | 0/24 (0.0%) | 102 |
| MIR441 | 11669.m 05042 | Os03g50 070 | expressed protein | [1047, 1070] | 24 | 21/24 (87.5%) | 0/24 (0.0%) | 93 |
| MIR441 | 11682.m | Os05g41 | expressed | [988, | 24 | 21/24 | 0/24 | 93 |

TABLE 4-continued

PATSCAN alignments of the new miRNAS
(SEQ ID NOS:36, 38, 40, 44, 46, 49, 52, 58, 66 and 68)
and their predicted targets in rice
(SEQ ID NOS:37, 39, 41-43, 45, 47-51, 53-57, 59-67 and 69).
miRNAs are presented as a reverse complemented form.

| | | | | | | | | |
|---|---|---|---|---|---|---|---|---|
| MIR441 | 11682.m 03939 | Os05g51 190 | protein | [1011] | 24 | 21/24 (87.5%) | 0/24 (0.0%) | 93 |
| MIR441 | 11682.m 04930 | Os05g51 140 | expressed protein | [1543, 1566] | 24 | 21/24 (87.5%) | 0/24 (0.0%) | 93 |
| MIR441 | 11686.m 03687 | Os12g37 510 | UDP-glucoronosyl and UDP-glucosyl transferase | [1544, 1567] | 24 | 21/24 (87.5%) | 0/24 (0.%) | 93 |
| MIR441 | 11687.m 00089 | Os11g01 870 | expressed protein | [5345, 5368] | 24 | 21/24 (87.5%) | 0/24 (0.0%) | 93 |
| MIR436 | 11686.m 04227 | Os12g42 390 | hypothetical protein | [12, 32] | 21 | 21/21 (100.0%) | 0/21 (0.0%) | 105 |
| MIR436 | 11686.m 04226 | Os12g42 380 | expressed protein | [235, 255] | 21 | 20/21 (95.2%) | 0/21 (0.0%) | 96 |
| MIR444 | 11668.m 04852 | Os02g49 840 | SRF-type transcription factor (DNA-binding and dimerisation domain), putative | [403, 423] | 21 | 21/21 (100.0%) | 0/21 (0.0%) | 105 |

| miRNA | Needle Alignment | | | | |
|---|---|---|---|---|---|
| MIR443 | P101-G11 | 1 | TCCAGATTTATTGTATTGTGAT | 22 |
| | | | \|\|.\|\|\|\|\|.\|\|\|\|\|\|.\|\|\|\| | |
| | 11687.m04039 | 1 | TCTAGATTTTTTGTATTATGAT | 22 |
| MIR445 | P103-F2 | 1 | ATCGGATGTTTATACACTAATTTA | 24 |
| | | | \|\|\|\|\|\|\|\|\|\|..\|\|.\|\|\|\|\|\|\|\| | |
| | 11680.m05074 | 1 | ATCGGATGTTTGGACGCTAATTTA | 24 |
| MIR446 | P105-E11 | 1 | CCATTTCCCATATTCATATTGATG | 24 |
| | | | .\|\|\|\|\|\|\|\|\|.\|\|\|\|\|\|\|\|\|\|\|\|\| | |
| | 11668.m04341 | 1 | GCATTTCCCACATTCATATTGATG | 24 |
| MIR446 | P105-E11 | 1 | CCATTTCCCATATTCATATTGATG | 24 |
| | | | .\|\|\|\|\|\|\|\|\|.\|\|\|\|\|\|\|\|\|\|\|\|\| | |
| | 11674.m00582 | 1 | GCATTTCCCACATTCATATTGATG | 24 |
| MIR446 | P105-E11 | 1 | CCATTTCCCATATTCATATTGATG | 24 |
| | | | .\|\|\|\|\|\|\|\|\|\|\|\|\|\|\|\|\|\|\|\|.\|\|\| | |
| | 11680.m01730 | 1 | GCATTTCCCATATTCATATTAATG | 24 |
| MIR446 | P105-E11 | 1 | CCATTTCCCATATTCATATTGATG | 24 |
| | | | .\|\|\|\|\|\|\|\|\|.\|\|\|\|\|\|\|\|\|\|\|\|\| | |
| | 11680.m01945 | 1 | GCATTTCCCACATTCATATTGATG | 24 |
| MIR446 | P05-E11 | 1 | CCATTTCCCATATTCATATTGATG | 24 |
| | | | .\|\|\|\|\|\|\|\|\|.\|\|\|\|.\|\|\|\|\|\|\|\|\| | |
| | 11682.m03939 | 1 | GCATTTCCCACATTCGTATTGATG | 24 |
| MIR446 | p105-E11 | 1 | CCATTTCCCATATTCATATTGATG | 24 |
| | | | .\|\|\|\|\|\|\|\|\|.\|\|\|\|.\|\|\|\|\|\|\|\|\| | |
| | 11682.m04930 | 1 | GCATTTCCCACATTCGTATTGATG | 24 |
| MIR437 | P14-F8 | 1 | AAGTCAAACTTCTCTAACTTT | 21 |
| | | | \|\|\|\|\|\|\|\|.\|\|\|\|\|\|\|\|\|\|\|\| | |
| | 11680.m04605 | 1 | AAGTCAAATTTCTCTAACTTT | 21 |
| MIR437 | P14-F8 | 1 | AAGTCAAACTTCTCTAACTTT | 21 |
| | | | \|\|\|\|\|\|\|\|.\|\|\|\|\|\|\|\|\|\|\|\| | |
| | 11680.m04606 | 1 | AAGTCAAATTTCTCTAACTTT | 21 |
| MIR390 | P28-A2 | 1 | GGCGCTATCCCTCCTGAGCTT | 21 |
| | | | \|\|\|.\|.\|\|\|\|\|\|\|\|\|\|\|\|\|.\|\| | |
| | 11674.m03433 | 1 | GGCACAATCCCTCCTGAGATT | 21 |
| MIR390 | P28-A2 | 1 | GGCGCTATCCCTCCTGAGCTT | 21 |
| | | | \|\|\|.\|\|.\|\|\|\|.\|\|\|\|\|\|\|\|\|\|\| | |
| | 11687.m03320 | 1 | GGCACTGTCCCTTCTGAGCTT | 21 |

TABLE 4-continued

PATSCAN alignments of the new miRNAS
(SEQ ID NOS:36, 38, 40, 44, 46, 49, 52, 58, 66 and 68)
and their predicted targets in rice
(SEQ ID NOS:37, 39, 41-43, 45, 47-51, 53-57, 59-67 and 69).
miRNAs are presented as a reverse complemented form.

| | | | | |
|---|---|---|---|---|
| MIR439 | P28-E3 | 1 | TCGAACAACCGCGGTTCGACA | 21 |
| | | | ||||||||||||||||||||| | |
| | 11667.m02576 | 1 | TCGAACAACCGCGGTTCGACA | 21 |
| MIR439 | P28-E3 | 1 | TCGAACAACCGCGGTTCGACA | 21 |
| | | | |||||||||||.||||||||| | |
| | 11680.m01869 | 1 | TCGAACAACCGCAGTTCGACA | 21 |
| MIR439 | P28-E3 | 1 | TCGAACAACCGCGGTTCGACA | 21 |
| | | | ||||||..||||.||||||||| | |
| | 11668.m02918 | 1 | TCGAACTGCCGCAGTTCGACA | 21 |
| MIR396d | P33-D7 | 1 | CAGTTCAAGAAAGCCTGTGGA | 21 |
| | | | |.||||||||||||||||||| | |
| | 11668.m04403 | 1 | CCGTTCAAGAAAGCCTGTGGA | 21 |
| MIR396d | p33-D7 | 1 | CAGTTCAAGAAAGCCTGTGGA | 21 |
| | | | |.||||||||||||||||||| | |
| | 11668.m04580 | 1 | CCGTTCAAGAAAGCCTGTGGA | 21 |
| MIR396d | P33-D7 | 1 | CAGTTCAAGAAAGCCTGTGGA | 21 |
| | | | |.||||||||||||||||||| | |
| | 11668.m05272 | 1 | CCGTTCAAGAAAGCCTGTGGA | 21 |
| MIR396d | P33-D7 | 1 | CAGTTCAAGAAAGCCTGTGGA | 21 |
| | | | |.||||||||||||||||||| | |
| | 11669.m04718 | 1 | CCGTTCAAGAAAGCCTGTGGA | 21 |
| MIR396d | P33-D7 | 1 | CAGTTCAAGAAAGCCTGTGGA | 21 |
| | | | |.||||||||||||||||||| | |
| | 11670.m04996 | 1 | CCGTTCAAGAAAGCCTGTGGA | 21 |
| MIR396d | P33-D7 | 1 | CAGTTCAAGAAAGCCTGTGGA | 21 |
| | | | |.||||||||||||||||||| | |
| | 11670.m04997 | 1 | CCGTTCAAGAAAGCCTGTGGA | 21 |
| MIR396d | P33-D7 | 1 | CAGTTCAAGAAAGCCTGTGGA | 21 |
| | | | |.||||||||||||||||||| | |
| | 11670.m04998 | 1 | CCGTTCAAGAAAGCCTGTGGA | 21 |
| MIR396d | P33-D7 | 1 | CAGTTCAAGAAAGCCTGTGGA | 21 |
| | | | |.||||||||||||||||||| | |
| | 11680.m00165 | 1 | CCGTTCAAGAAAGCCTGTGGA | 21 |
| MIR396d | P33-D7 | 1 | CAGTTCAAGAAAGCCTGTGGA | 21 |
| | | | |.||||||||||||||||||| | |
| | 11680.m00166 | 1 | CCGTTCAAGAAAGCCTGTGGA | 21 |
| MIR396d | P33-D7 | 1 | CAGTTCAAGAAAGCCTGTGGA | 21 |
| | | | |.||||||||||||||||||| | |
| | 11680.m00999 | 1 | CCGTTCAAGAAAGCCTGTGGA | 21 |
| MIR396d | P33-D7 | 1 | CAGTTCAAGAAAGCCTGTGGA | 21 |
| | | | |.|||||||||||||.||||| | |
| | 11669.m05248 | 1 | CCGTTCAAGAAAGCATGTGGA | 21 |
| MIR396d | P33-D7 | 1 | CAGTTCAAGAAAGCCTGTGGA | 21 |
| | | | |..|||||||||||||||||| | |
| | 11670.m02258 | 1 | CCTTTCAAGAAAGCCTGTGGA | 21 |
| MIR396d | P33-D7 | 1 | CAGTTCAAGAAAGCCTGTGGA | 21 |
| | | | |.||||||||||||||.|||| | |
| | 11670.m04758 | 1 | CCGTTCAAGAAAGCCTATGGA | 21 |
| MIR396d | P33-D7 | 1 | CAGTTCAAGAAAGCCTGTGGA | 21 |
| | | | |.|||||||||||||.||||| | |
| | 11686.m02909 | 1 | CCGTTCAAGAAAGCATGTGGA | 21 |
| MIR396d | P33-D7 | 1 | CAGTTCAAGAAAGCCTGTGGA | 21 |
| | | | | |||||||||||||.||||| | |
| | 11687.m03206 | 1 | TC-GTTCAAGAAAGCATGTGGA | 21 |

TABLE 4-continued

PATSCAN alignments of the new miRNAS
(SEQ ID NOS:36, 38, 40, 44, 46, 49, 52, 58, 66 and 68)
and their predicted targets in rice
(SEQ ID NOS:37, 39, 41-43, 45, 47-51, 53-57, 59-67 and 69).
miRNAs are presented as a reverse complemented form.

```
MIR441    P72-C9         1  TTTCCCACATTTATATTGATGGTA  24
                            ||||.||||||||||||||||.||
          11667.m06876   1  TTTCTCACATTTATATTGATGTTA  24

MIR441    P72-C9         1  TTTCCCACATTTATATTGATGGTA  24
                            ||||||||||.|||||||||||.||
          11668.m04341   1  TTTCCCACATTCATATTGATGTTA  24

MIR441    P72-C9         1  TTTCCCACATTTATATTGATGGTA  24
                            ||||||||.|||||||||||||.||
          11674.m00346   1  TTTCCCAGATTTATATTGATGCTA  24

MIR441    P72-C9         1  TTTCCCACATTTATATTGATGGTA  24
                            ||||||||||.|||||||||||.||
          11674.m00582   1  TTTCCCACATTCATATTGATGTTA  24

MIR441    P72-C9         1  TTTCCCACATTTATATTGATGGTA  24
                            ||||||||||.|||||||||||.||
          11680.m01945   1  TTTCCCACATTCATATTGATGCTA  24

MIR441    P72-C9         1  TTTCCCACATTTATATTGATGGTA  24
                            |||.||||||.|||||||||||.||
          11669.m05042   1  TTTTCCACATTCATATTGATGTTA  24

MIR441    P72-C9         1  TTTCCCACATTTATATTGATGGTA  24
                            ||||||||||..|||||||||.||
          11682.m03939   1  TTTCCCACATTCGTATTGATGTTA  24

MIR441    P72-C9         1  TTTCCCACATTTATATTGATGGTA  24
                            ||||||||||..|||||||||.||
          11682.m04930   1  TTTCCCACATTCGTATTGATGTTA  24

MIR441    P72-C9         1  TTTCCCACATTTATATTGATGGTA  24
                            |||.|||||.|||||||||||.||
          11686.m03687   1  TTTTCCACATATATATTGATGTTA  24

MIR441    P72-C9         1  TTTCCCACATTTATATTGATGGTA  24
                            ||||..|||||||||||||||.||
          11687.m00089   1  TTTCTTACATTTATATTGATGTTA  24

MIR436    P8-D2          1  GGGAGAAAGTGCACTCTCTCA    21
                            |||||||||||||||||||||
          11686.m04227   1  GGGAGAAAGTGCACTCTCTCA    21

MIR436    P8-D2          1  GGGAGAAAGTGCACTCTCTCA    21
                            |||||||||.|||||||||||
          11686.m04226   1  GGGAGAAAATGCACTCTCTCA    21

MIR444    P95-G4         1  GCAGCAAGCTTGAGGCAGCAA    21
                            |||||||||||||||||||||
          11668.m04852   1  GCAGCAAGCTTGAGGCAGCAA    21
```

TABLE 5

Potential new miRNAs from rice. Frequency of cloning is indicated in parentheses after the miRNA sequences.

| miRNA | Sequence (5' to 3') (SEQ ID NOS:70-74) | RNA blot | size (nt) | No. of loci | Chr. | Foldback (5'/3') | Conservation intergenic/intron/exon | Osi | Zm | At | Pt |
|---|---|---|---|---|---|---|---|---|---|---|---|
| P18-F1 | UCUCUCUCUCCCUUGAAGGC (1) | — | 20 | 1 | 11 | 5' | intergenic | + | − | − | − |
| P20-A11 | CGCGAGGUACCGAUACCUCGA (1) | — | 21 | 1 | 6 | 3' | JNBa0052G07.19 (s) | + | − | − | − |
| P83-E9 | UCAGUGUCAUACGAUAUGGCGC (1) | — | 22 | 1 | 8 | 3' | intergenic | − | − | − | − |
| P92-A7 | CAUCCUAAAAUAUAAGCAGUUUUAG (1) | — | 25 | 1 | 11 | 5' | intergenic | + | − | − | − |
| P101-H12 | AUAGUGAACACCGAUAUGCGU (1) | — | 21 | 1 | 11 | 3' | intergenic | + | − | − | − |

Osi: *Oryza sativa* subspecies *indica*; Zm: *Zea mays*; At: *Arabidopsis thaliana*; Pt: *Populus trichocarpa*

What is claimed is:
1. An isolated miRNA set forth in SEQ ID NO:12.
2. A recombinant expression cassette encoding the miRNA of claim 1.
3. A transgenic plant comprising the expression cassette of claim 2.
4. A method of inhibiting down-regulation of a target coding region, wherein the coding region comprises a polynucleotide sequence encoding SEQ ID NO:12 the method comprising mutating at least one nucleotide in the polynucleotide sequence to render the coding region resistant to miRNA mediated down-regulation.

* * * * *

SEQUENCE LISTING

<160> NUMBER OF SEQ ID NOS: 150

<210> SEQ ID NO 1
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) miR390

<400> SEQUENCE: 1
aagcucagga gggauagcgc c                                                   21

<210> SEQ ID NO 2
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) miR396d,e (P33-D7)

<400> SEQUENCE: 2
uccacaggcu uucuugaacu g                                                   21

<210> SEQ ID NO 3
<211> LENGTH: 20
<212> TYPE: RNA
<213> ORGANISM: Artificial Sequence
<220> FEATURE:
<223> OTHER INFORMATION: Indica rice (Oryza sativa spp. indica) microRNA
      (miRNA) miR435

<400> SEQUENCE: 3
uuauccggua uuggaguuga                                                     20

<210> SEQ ID NO 4
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) miR436

<400> SEQUENCE: 4
ugagagagug cacuuucucc c                                                   21

<210> SEQ ID NO 5
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) miR437

<400> SEQUENCE: 5
aaaguuagag aaguuugacu u                                                   21

<210> SEQ ID NO 6
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) miR438

<400> SEQUENCE: 6
uucccacgcg uuauagugaa a                                                   21

<210> SEQ ID NO 7
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) miR439a-j (P28-E3)

<400> SEQUENCE: 7
ugucgaaccg cgguuguucg a                                                   21

<210> SEQ ID NO 8
<211> LENGTH: 24
<212> TYPE: RNA
<213> ORGANISM: Artificial Sequence
<220> FEATURE:
<223> OTHER INFORMATION: Indica rice (Oryza sativa spp. indica) microRNA
      (miRNA) miR440

<400> SEQUENCE: 8
agugucuccu gaugaucggg acaa                                                24

<210> SEQ ID NO 9
<211> LENGTH: 24
<212> TYPE: RNA
<213> ORGANISM: Artificial Sequence
<220> FEATURE:
<223> OTHER INFORMATION: Indica rice (Oryza sativa spp. indica) microRNA
      (miRNA) miR441a-c

<400> SEQUENCE: 9
uaccaucaau auaaaugugg gaaa                                                24

<210> SEQ ID NO 10
<211> LENGTH: 24
<212> TYPE: RNA
<213> ORGANISM: Artificial Sequence
<220> FEATURE:
<223> OTHER INFORMATION: Indica rice (Oryza sativa spp. indica) microRNA
      (miRNA) miR442

<400> SEQUENCE: 10
ugacguguaa auugcgagac gaau                                                24

<210> SEQ ID NO 11
<211> LENGTH: 22
<212> TYPE: RNA
<213> ORGANISM: Artificial Sequence
<220> FEATURE:
<223> OTHER INFORMATION: Indica rice (Oryza sativa spp. indica) microRNA
      (miRNA) miR443

<400> SEQUENCE: 11
aucacaauac aauaaaucug ga                                                  22

<210> SEQ ID NO 12
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) miR444 and homolog in wheat and barley

<400> SEQUENCE: 12

-continued uugcugccuc aagcuugcug c                                    21

<210> SEQ ID NO 13
<211> LENGTH: 24
<212> TYPE: RNA
<213> ORGANISM: Artificial Sequence
<220> FEATURE:
<223> OTHER INFORMATION: Indica rice (Oryza sativa spp. indica) microRNA
      (miRNA) miR445a-i

<400> SEQUENCE: 13
uaaauuagug uauaaacauc cgau                                 24

<210> SEQ ID NO 14
<211> LENGTH: 24
<212> TYPE: RNA
<213> ORGANISM: Artificial Sequence
<220> FEATURE:
<223> OTHER INFORMATION: Indica rice (Oryza sativa spp. indica) microRNA
      (miRNA) miR446

<400> SEQUENCE: 14
caucaauaug aauaugggaa augg                                 24

<210> SEQ ID NO 15
<211> LENGTH: 20
<212> TYPE: RNA
<213> ORGANISM: Artificial Sequence
<220> FEATURE:
<223> OTHER INFORMATION: Indica rice (Oryza sativa spp. indica) microRNA
      (miRNA) OsmiR156a-j

<400> SEQUENCE: 15
ugacagaaga gagugagcac                                      20

<210> SEQ ID NO 16
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) OsmiR156k,l

<400> SEQUENCE: 16
ugacagaaga gagugagcac a                                    21

<210> SEQ ID NO 17
<211> LENGTH: 20
<212> TYPE: RNA
<213> ORGANISM: Artificial Sequence
<220> FEATURE:
<223> OTHER INFORMATION: Indica rice (Oryza sativa spp. indica) microRNA
      (miRNA) OsmiR159a,b

<400> SEQUENCE: 17
uuuggauuga agggagcucu                                      20

<210> SEQ ID NO 18
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) OsmiR159c

<400> SEQUENCE: 18
uuggauugaa gggagcucug c                                    21

<210> SEQ ID NO 19
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
   (miRNA) OsmiR160

<400> SEQUENCE: 19
ugccuggcuc ccuguaugcc a					21

<210> SEQ ID NO 20
<211> LENGTH: 22
<212> TYPE: RNA
<213> ORGANISM: Artificial Sequence
<220> FEATURE:
<223> OTHER INFORMATION: Indica rice (Oryza sativa spp. indica) microRNA
   (miRNA) OsmiR164

<400> SEQUENCE: 20
auggagaagc agggcacgug ca					22

<210> SEQ ID NO 21
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
   (miRNA) OsmiR166a-f

<400> SEQUENCE: 21
ucggaccagg cuucauuccc c					21

<210> SEQ ID NO 22
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
   (miRNA) OsmiR167a,b,c

<400> SEQUENCE: 22
ugaagcugcc agcaugaucu a					21

<210> SEQ ID NO 23
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
   (miRNA) OsmiR167d-i

<400> SEQUENCE: 23
ugaagcugcc agcaugaucu g					21

<210> SEQ ID NO 24
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
   (miRNA) OsmiR168a

<400> SEQUENCE: 24
ucgcuuggug cagaucggga c					21

<210> SEQ ID NO 25
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) OsmiR169b,c

<400> SEQUENCE: 25
cagccaagga ugacuugccg g                                        21

<210> SEQ ID NO 26
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) OsmiR169f,g

<400> SEQUENCE: 26
uagccaagga ugacuugccu a                                        21

<210> SEQ ID NO 27
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) OsmiR169h-m

<400> SEQUENCE: 27
uagccaagga ugacuugccu g                                        21

<210> SEQ ID NO 28
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) OsmiR171a-f

<400> SEQUENCE: 28
ugauugagcc gugccaauau c                                        21

<210> SEQ ID NO 29
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) OsmiR171g

<400> SEQUENCE: 29
gaggugagcc gugccaauau c                                        21

<210> SEQ ID NO 30
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) OsmiR172a

<400> SEQUENCE: 30
agaaucuuga ugaugcugca u                                        21

<210> SEQ ID NO 31
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) OsmiR393

<400> SEQUENCE: 31
uccaagggga ucgcauugau c                                                 21

<210> SEQ ID NO 32
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) OsmiR397b

<400> SEQUENCE: 32
uuauugagug cagcguugau g                                                 21

<210> SEQ ID NO 33
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) OsmiR398

<400> SEQUENCE: 33
uguguucuca ggucgccccu g                                                 21

<210> SEQ ID NO 34
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) OsmiR399a

<400> SEQUENCE: 34
ugccaaagga gaauugcccu g                                                 21

<210> SEQ ID NO 35
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) OsmiR408

<400> SEQUENCE: 35
cugcacugcc ucuucccugg c                                                 21

<210> SEQ ID NO 36
<211> LENGTH: 22
<212> TYPE: DNA
<213> ORGANISM: Artificial Sequence
<220> FEATURE:
<223> OTHER INFORMATION: Indica rice (Oryza sativa spp. indica) microRNA
      (miRNA) miR443 (P101-G11)

<400> SEQUENCE: 36
tccagattta ttgtattgtg at                                                22

<210> SEQ ID NO 37

-continued

<210> SEQ ID NO 37
<211> LENGTH: 22
<212> TYPE: DNA
<213> ORGANISM: Artificial Sequence
<220> FEATURE:
<223> OTHER INFORMATION: Indica rice (Oryza sativa spp. indica) microRNA
      (miRNA) miR443 (P101-G11) predicted target
      11687.m04039

<400> SEQUENCE: 37 tctagattttt ttgtattatg at                                             22

<210> SEQ ID NO 38
<211> LENGTH: 24
<212> TYPE: DNA
<213> ORGANISM: Artificial Sequence
<220> FEATURE:
<223> OTHER INFORMATION: Indica rice (Oryza sativa spp. indica) microRNA
      (miRNA) miR445 (P103-F2)

<400> SEQUENCE: 38
atcggatgtt tatacactaa ttta                                            24

<210> SEQ ID NO 39
<211> LENGTH: 24
<212> TYPE: DNA
<213> ORGANISM: Artificial Sequence
<220> FEATURE:
<223> OTHER INFORMATION: Indica rice (Oryza sativa spp. indica) microRNA
      (miRNA) miR445 (P103-F2) predicted target
      11680.m05074

<400> SEQUENCE: 39
atcggatgtt tggacgctaa ttta                                            24

<210> SEQ ID NO 40
<211> LENGTH: 24
<212> TYPE: DNA
<213> ORGANISM: Artificial Sequence
<220> FEATURE:
<223> OTHER INFORMATION: Indica rice (Oryza sativa spp. indica) microRNA
      (miRNA) miR446 (P105-E11)

<400> SEQUENCE: 40
ccatttccca tattcatatt gatg                                            24

<210> SEQ ID NO 41
<211> LENGTH: 24
<212> TYPE: DNA
<213> ORGANISM: Artificial Sequence
<220> FEATURE:
<223> OTHER INFORMATION: Indica rice (Oryza sativa spp. indica) microRNA
      (miRNA) miR446 (P105-E11) predicted target
      1168.m04341, 11674.m00582 and 11680.m01945

<400> SEQUENCE: 41
gcatttccca cattcatatt gatg                                            24

<210> SEQ ID NO 42
<211> LENGTH: 24
<212> TYPE: DNA
<213> ORGANISM: Artificial Sequence
<220> FEATURE:
<223> OTHER INFORMATION: Indica rice (Oryza sativa spp. indica) microRNA
      (miRNA) miR446 (P105-E11) predicted target
      11680.m01730

<400> SEQUENCE: 42
gcatttccca tattcatatt aatg                                            24

-continued

<210> SEQ ID NO 43
<211> LENGTH: 24
<212> TYPE: DNA
<213> ORGANISM: Artificial Sequence
<220> FEATURE:
<223> OTHER INFORMATION: Indica rice (Oryza sativa spp. indica) microRNA
    (miRNA) miR446 (P105-E11) predicted target
    11682.m03939 and 11682.m04930

<400> SEQUENCE: 43
gcatttccca cattcgtatt gatg                                          24

<210> SEQ ID NO 44
<211> LENGTH: 21
<212> TYPE: DNA
<213> ORGANISM: Artificial Sequence
<220> FEATURE:
<223> OTHER INFORMATION: Indica rice (Oryza sativa spp. indica) microRNA
    (miRNA) miR437 (P14-F8)

<400> SEQUENCE: 44
aagtcaaact tctctaactt t                                             21

<210> SEQ ID NO 45
<211> LENGTH: 21
<212> TYPE: DNA
<213> ORGANISM: Artificial Sequence
<220> FEATURE:
<223> OTHER INFORMATION: Indica rice (Oryza sativa spp. indica) microRNA
    (miRNA) miR437 (P14-F8) predicted target
    11680.m04605 and 11680.m04606

<400> SEQUENCE: 45
aagtcaaatt tctctaactt t                                             21

<210> SEQ ID NO 46
<211> LENGTH: 21
<212> TYPE: DNA
<213> ORGANISM: Artificial Sequence
<220> FEATURE:
<223> OTHER INFORMATION: Indica rice (Oryza sativa spp. indica) microRNA
    (miRNA) miR390 (P28-A2)

<400> SEQUENCE: 46
ggcgctatcc ctcctgagct t                                             21

<210> SEQ ID NO 47
<211> LENGTH: 21
<212> TYPE: DNA
<213> ORGANISM: Artificial Sequence
<220> FEATURE:
<223> OTHER INFORMATION: Indica rice (Oryza sativa spp. indica) microRNA
    (miRNA) miR390 (P28-A2) predicted target
    11674.m03433

<400> SEQUENCE: 47
ggcacaatcc ctcctgagat t                                             21

<210> SEQ ID NO 48
<211> LENGTH: 21
<212> TYPE: DNA
<213> ORGANISM: Artificial Sequence
<220> FEATURE:
<223> OTHER INFORMATION: Indica rice (Oryza sativa spp. indica) microRNA
    (miRNA) miR390 (P28-A2) predicted target
    11687.m03320

<400> SEQUENCE: 48
ggcactgtcc cttctgagct t                                          21

<210> SEQ ID NO 49
<211> LENGTH: 21
<212> TYPE: DNA
<213> ORGANISM: Artificial Sequence
<220> FEATURE:
<223> OTHER INFORMATION: Indica rice (Oryza sativa spp. indica) microRNA
      (miRNA) miR439 (P28-E3) and predicted target
      11667.m02576

<400> SEQUENCE: 49
tcgaacaacc gcggttcgac a                                          21

<210> SEQ ID NO 50
<211> LENGTH: 21
<212> TYPE: DNA
<213> ORGANISM: Artificial Sequence
<220> FEATURE:
<223> OTHER INFORMATION: Indica rice (Oryza sativa spp. indica) microRNA
      (miRNA) miR439 (P28-E3) predicted target
      11680.m01869

<400> SEQUENCE: 50
tcgaacaacc gcagttcgac a                                          21

<210> SEQ ID NO 51
<211> LENGTH: 21
<212> TYPE: DNA
<213> ORGANISM: Artificial Sequence
<220> FEATURE:
<223> OTHER INFORMATION: Indica rice (Oryza sativa spp. indica) microRNA
      (miRNA) miR439 (P28-E3) predicted target
      11668.m02918

<400> SEQUENCE: 51
tcgaactgcc gcagttcgac a                                          21

<210> SEQ ID NO 52
<211> LENGTH: 21
<212> TYPE: DNA
<213> ORGANISM: Artificial Sequence
<220> FEATURE:
<223> OTHER INFORMATION: Indica rice (Oryza sativa spp. indica) microRNA
      (miRNA) miR396d (P33-D7)

<400> SEQUENCE: 52
cagttcaaga aagcctgtgg a                                          21

<210> SEQ ID NO 53
<211> LENGTH: 21
<212> TYPE: DNA
<213> ORGANISM: Artificial Sequence
<220> FEATURE:
<223> OTHER INFORMATION: Indica rice (Oryza sativa spp. indica) microRNA
      (miRNA) miR396d (P33-D7) predicted target 11668.m04403,
      11668.m04580, 11668.m05272, 11669.m04718, 11670.m04996,
      11670.m04997, 11670.m04998, 11680.m00165, 11680.m00166 and
      11680.m00999

<400> SEQUENCE: 53
ccgttcaaga aagcctgtgg a                                          21

<210> SEQ ID NO 54
<211> LENGTH: 21
<212> TYPE: DNA

```
<213> ORGANISM: Artificial Sequence
<220> FEATURE:
<223> OTHER INFORMATION: Indica rice (Oryza sativa spp. indica) microRNA
      (miRNA) miR396d (P33-D7) predicted target
      11669.m05248 and 11686.m02909

<400> SEQUENCE: 54
ccgttcaaga aagcatgtgg a                                                   21

<210> SEQ ID NO 55
<211> LENGTH: 21
<212> TYPE: DNA
<213> ORGANISM: Artificial Sequence
<220> FEATURE:
<223> OTHER INFORMATION: Indica rice (Oryza sativa spp. indica) microRNA
      (miRNA) miR396d (P33-D7) predicted target
      11670.m02258

<400> SEQUENCE: 55
cctttcaaga aagcctgtgg a                                                   21

<210> SEQ ID NO 56
<211> LENGTH: 21
<212> TYPE: DNA
<213> ORGANISM: Artificial Sequence
<220> FEATURE:
<223> OTHER INFORMATION: Indica rice (Oryza sativa spp. indica) microRNA
      (miRNA) miR396d (P33-D7) predicted target
      11670.m04758

<400> SEQUENCE: 56
ccgttcaaga aagcctatgg a                                                   21

<210> SEQ ID NO 57
<211> LENGTH: 21
<212> TYPE: DNA
<213> ORGANISM: Artificial Sequence
<220> FEATURE:
<223> OTHER INFORMATION: Indica rice (Oryza sativa spp. indica) microRNA
      (miRNA) miR396d (P33-D7) predicted target
      11687.m03206

<400> SEQUENCE: 57
tcgttcaaga aagcatgtgg a                                                   21

<210> SEQ ID NO 58
<211> LENGTH: 24
<212> TYPE: DNA
<213> ORGANISM: Artificial Sequence
<220> FEATURE:
<223> OTHER INFORMATION: Indica rice (Oryza sativa spp. indica) microRNA
      (miRNA) miR441 (P72-C9)

<400> SEQUENCE: 58
tttcccacat ttatattgat ggta                                                24

<210> SEQ ID NO 59
<211> LENGTH: 24
<212> TYPE: DNA
<213> ORGANISM: Artificial Sequence
<220> FEATURE:
<223> OTHER INFORMATION: Indica rice (Oryza sativa spp. indica) microRNA
      (miRNA) miR441 (P72-C9) predicted target
      11667.m06876

<400> SEQUENCE: 59
tttctcacat ttatattgat gtta                                                24
```

<210> SEQ ID NO 60
<211> LENGTH: 24
<212> TYPE: DNA
<213> ORGANISM: Artificial Sequence
<220> FEATURE:
<223> OTHER INFORMATION: Indica rice (Oryza sativa spp. indica) microRNA
      (miRNA) miR441 (P72-C9) predicted target
      11668.m04341, 11674.m00582 and 11680.m01945

<400> SEQUENCE: 60
tttcccacat tcatattgat gtta                                         24

<210> SEQ ID NO 61
<211> LENGTH: 24
<212> TYPE: DNA
<213> ORGANISM: Artificial Sequence
<220> FEATURE:
<223> OTHER INFORMATION: Indica rice (Oryza sativa spp. indica) microRNA
      (miRNA) miR441 (P72-C9) predicted target
      11674.m00346

<400> SEQUENCE: 61
tttcccagat ttatattgat gcta                                         24

<210> SEQ ID NO 62
<211> LENGTH: 24
<212> TYPE: DNA
<213> ORGANISM: Artificial Sequence
<220> FEATURE:
<223> OTHER INFORMATION: Indica rice (Oryza sativa spp. indica) microRNA
      (miRNA) miR441 (P72-C9) predicted target
      11669.m05042

<400> SEQUENCE: 62 ttttcccacat tcatattgat gtta                                        24

<210> SEQ ID NO 63
<211> LENGTH: 24
<212> TYPE: DNA
<213> ORGANISM: Artificial Sequence
<220> FEATURE:
<223> OTHER INFORMATION: Indica rice (Oryza sativa spp. indica) microRNA
      (miRNA) miR441 (P72-C9) predicted target
      11682.m03939 and 11682.m04930

<400> SEQUENCE: 63
tttcccacat tcgtattgat gtta                                         24

<210> SEQ ID NO 64
<211> LENGTH: 24
<212> TYPE: DNA
<213> ORGANISM: Artificial Sequence
<220> FEATURE:
<223> OTHER INFORMATION: Indica rice (Oryza sativa spp. indica) microRNA
      (miRNA) miR441 (P72-C9) predicted target
      11686.m03687

<400> SEQUENCE: 64
ttttccacat atatattgat gtta                                         24

<210> SEQ ID NO 65
<211> LENGTH: 24
<212> TYPE: DNA
<213> ORGANISM: Artificial Sequence
<220> FEATURE:
<223> OTHER INFORMATION: Indica rice (Oryza sativa spp. indica) microRNA
      (miRNA) miR441 (P72-C9) predicted target
      11687.m00089

```
<400> SEQUENCE: 65
tttcttacat ttatattgat gtta                                             24

<210> SEQ ID NO 66
<211> LENGTH: 21
<212> TYPE: DNA
<213> ORGANISM: Artificial Sequence
<220> FEATURE:
<223> OTHER INFORMATION: Indica rice (Oryza sativa spp. indica) microRNA
      (miRNA) miR436 (P8-D2) and predicted target
      11686.m04227

<400> SEQUENCE: 66
gggagaaagt gcactctctc a                                                21

<210> SEQ ID NO 67
<211> LENGTH: 21
<212> TYPE: DNA
<213> ORGANISM: Artificial Sequence
<220> FEATURE:
<223> OTHER INFORMATION: Indica rice (Oryza sativa spp. indica) microRNA
      (miRNA) miR436 (P8-D2) predicted target
      11686.m04226

<400> SEQUENCE: 67
gggagaaaat gcactctctc a                                                21

<210> SEQ ID NO 68
<211> LENGTH: 21
<212> TYPE: DNA
<213> ORGANISM: Artificial Sequence
<220> FEATURE:
<223> OTHER INFORMATION: Indica rice (Oryza sativa spp. indica) microRNA
      (miRNA) miR444 (P95-G4) and predicted target
      11668.m04852

<400> SEQUENCE: 68
gcagcaagct tgaggcagca a                                                21

<210> SEQ ID NO 69
<211> LENGTH: 20
<212> TYPE: RNA
<213> ORGANISM: Artificial Sequence
<220> FEATURE:
<223> OTHER INFORMATION: Indica rice (Oryza sativa spp. indica) microRNA
      (miRNA) P18-F1

<400> SEQUENCE: 69
ucucucucuc ccuugaaggc                                                  20

<210> SEQ ID NO 70
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) P20-A11

<400> SEQUENCE: 70 cgcgaggguac cgauaccucg a                                               21

<210> SEQ ID NO 71
<211> LENGTH: 22
<212> TYPE: RNA
<213> ORGANISM: Artificial Sequence
<220> FEATURE:
```

<223> OTHER INFORMATION: Indica rice (Oryza sativa spp. indica) microRNA
      (miRNA) P83-E9

<400> SEQUENCE: 71
ucagugucau acgauauggc gc                                          22

<210> SEQ ID NO 72
<211> LENGTH: 25
<212> TYPE: RNA
<213> ORGANISM: Artificial Sequence
<220> FEATURE:
<223> OTHER INFORMATION: Indica rice (Oryza sativa spp. indica) microRNA
      (miRNA) P92-A7

<400> SEQUENCE: 72
cauccuaaaa uauaagcagu uuuag                                       25

<210> SEQ ID NO 73
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) P101-H12

<400> SEQUENCE: 73
auagugaaca ccgauaugcg u                                           21

<210> SEQ ID NO 74
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) OsmiR396a,b

<400> SEQUENCE: 74
uuccacagcu uucuugaacu g                                           21

<210> SEQ ID NO 75
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) OsmiR396c

<400> SEQUENCE: 75
uuccacagcu uucuugaacu u                                           21

<210> SEQ ID NO 76
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) OsmiR399j,k

<400> SEQUENCE: 76
ugccaaagga gaguugcccu a                                           21

<210> SEQ ID NO 77
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA

```
                (miRNA) OsmiR399e

<400> SEQUENCE: 77
ugccaaagga gauuugccca g                                              21

<210> SEQ ID NO 78
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) OsmiR399g

<400> SEQUENCE: 78
ugccaaagga gauuugcccg g                                              21

<210> SEQ ID NO 79
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) OsmiR399h

<400> SEQUENCE: 79
ugccaaagga gacuugccca g                                              21

<210> SEQ ID NO 80
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) OsmiR399d,i

<400> SEQUENCE: 80
ugccaaagga gagcugcccu g                                              21

<210> SEQ ID NO 81
<211> LENGTH: 22
<212> TYPE: RNA
<213> ORGANISM: Artificial Sequence
<220> FEATURE:
<223> OTHER INFORMATION: Indica rice (Oryza sativa spp. indica) microRNA
      (miRNA) P7-A07

<400> SEQUENCE: 81
ugccaaugga guaguugccc ug                                             22

<210> SEQ ID NO 82
<211> LENGTH: 127
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR444 from host transcript J033125N22

<400> SEQUENCE: 82
gcaauugggg gcagcaagcu agagguggca acugcauaau uugcaagaaa uuguuggcug    60
aagaucauac cgaugauauu cuugcaaguu augcaguugc ugccucaagc uugcugccuc   120
cuguugc                                                             127

<210> SEQ ID NO 83
<211> LENGTH: 21
```

```
<212> TYPE: RNA
<213> ORGANISM: Artificial Sequence
<220> FEATURE:
<223> OTHER INFORMATION: Indica rice (Oryza sativa spp. indica) microRNA
      (miRNA) miR444 homolog in maize, sorghum and
      sugarcane

<400> SEQUENCE: 83
uuguugccuc aagcuugcug c                                              21

<210> SEQ ID NO 84
<211> LENGTH: 127
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back structure for
      miR444

<400> SEQUENCE: 84
gcaauugggg gcagcaagcu agagguggca acugcauaau uugcaagaaa uuguuggcug     60
aagaucauac cgaugauauu cuugcaaguu augcaguugc ugccucaagc uugcugccuc    120
cguugc                                                              127

<210> SEQ ID NO 85
<211> LENGTH: 138
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back structure for
      miR444 homolog in wheat

<400> SEQUENCE: 85
ggcaccgagc augaggcaac aacugcauua cuugcgggga aggcgcaagu aggacaccug     60
cauuacuugc aaacaaggcg caccauacuu guggcuuucu ugcaagucau gcaguugcug    120
ccucaagcuu gcugccuc                                                  138

<210> SEQ ID NO 86
<211> LENGTH: 168
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back structure for
      miR444 homolog in barley

<400> SEQUENCE: 86
gauacgcaug uggcggcacc aagcaugaag caacaacugc aguacuugug gggaaagcac     60
aaguaggaca ccaacauuac cugcaagcaa gacgcccaua cuuguggcuu ucuugcaagu    120
cgugcaguug cugccucaag cuugcugccu cccuuugcca aagcuauc                 168

<210> SEQ ID NO 87
<211> LENGTH: 115
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back structure for
      miR444 homolog in maize

<400> SEQUENCE: 87
ggcaccaagc augaggcagg aacugcauua cuugcaagaa agucacaaaa ucaauugcag     60
```

```
                                              -continued
gacauacuug ugguuuucuu gcaaguugug caguuguugc cucaagcuug cugcc        115

<210> SEQ ID NO 88
<211> LENGTH: 148
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back structure for
      miR444 homolog in sorghum

<400> SEQUENCE: 88
ggcaccaagc augaggcagg aacugcauua cuugcaagaa agucacaagc ucauuucaag     60
auggcucucu aaacuuugga gaaucaauug cagaccauac uuguggcuuu cuugcaaguu    120
gugcaguugu ugccucaagc uugcugcc                                      148

<210> SEQ ID NO 89
<211> LENGTH: 145
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back structure for
      miR444 homolog in sugarcane

<400> SEQUENCE: 89
guauugcaua ugguggcacc aagcaugagg caggaacugc auuacuugca agaaagucac     60
aaaaucaauu gcaggaucau acuuguggcu uucuugcaag uugugcaguu guugccucaa    120
gcuugcugcc ucccuuugcc agagc                                         145

<210> SEQ ID NO 90
<211> LENGTH: 155
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR436

<400> SEQUENCE: 90
cuuuagaauc ucuugagaga gugcacuuuc ucccucuccu gccaucagua gugccuuuau     60
uuucgcuugg uuuccgcauc aucagguggg aaaaagcaag ggcacuguug cuggcaggau    120
agggagaaaa ugcacucucu caagagauuc uaaag                              155

<210> SEQ ID NO 91
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) OsmiR439 (P28-E3) predicted target
      11667.m02576

<400> SEQUENCE: 91
ucgaacaacc gcgguucgac a                                              21

<210> SEQ ID NO 92
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) OsmiR439 (P28-E3) predicted target
      11667.m02576
```

<400> SEQUENCE: 92
ucgaacaacc acaguucgac a							21

<210> SEQ ID NO 93
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
    (miRNA) miR408 predicted target 7448.m00137

<400> SEQUENCE: 93
cccagggaag aggcagugca g							21

<210> SEQ ID NO 94
<211> LENGTH: 24
<212> TYPE: RNA
<213> ORGANISM: Artificial Sequence
<220> FEATURE:
<223> OTHER INFORMATION: Indica rice (Oryza sativa spp. indica) microRNA
    (miRNA) P28-A2 predicted target 11668.m00935

<400> SEQUENCE: 94
ggcgcuaucc cuucugagcu augc						24

<210> SEQ ID NO 95
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
    (miRNA) P28-A2

<400> SEQUENCE: 95
aagcucagga gggauagcgc c							21

<210> SEQ ID NO 96
<211> LENGTH: 24
<212> TYPE: RNA
<213> ORGANISM: Artificial Sequence
<220> FEATURE:
<223> OTHER INFORMATION: Indica rice (Oryza sativa spp. indica) microRNA
    (miRNA) P95-G4 predicted target 11668.m04852

<400> SEQUENCE: 96
ggcagcaagc uugaggcagc aacu						24

<210> SEQ ID NO 97
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
    (miRNA) P95-G4

<400> SEQUENCE: 97
uugcugccuc aagcuugcug c							21

<210> SEQ ID NO 98
<211> LENGTH: 22
<212> TYPE: RNA
<213> ORGANISM: Artificial Sequence
<220> FEATURE:
<223> OTHER INFORMATION: Indica rice (Oryza sativa spp. indica) microRNA
    (miRNA) P8-D2 predicted target 11686.m04227

<400> SEQUENCE: 98
agggagaaag ugcacucucu ca          22

<210> SEQ ID NO 99
<211> LENGTH: 21
<212> TYPE: RNA
<213> ORGANISM: Artificial Sequence
<220> FEATURE:
<223> OTHER INFORMATION: Indica rice (Oryza sativa spp. indica) microRNA
      (miRNA) P8-D2

<400> SEQUENCE: 99
ugagagagug cacuuucucc c           21

<210> SEQ ID NO 100
<211> LENGTH: 255
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR435

<400> SEQUENCE: 100
cuacucuucu uagucuacgu uucaucucuc aacccaaaa cuggacaaaa caugucccuc          60
aucuucccua gcacuaguuu agagugguuu uugcccaugu ggacuacuug gcuagucgac        120
uugcauaaca aaugacaugu acagggugag cuaagagcca ugugcgaaaa uugccuugaa        180
uuaggauagu uuagggacau guuuuauccg guauuggagu ugagggauga aaauuggacc        240
aagucaagag uuuau                                                          255

<210> SEQ ID NO 101
<211> LENGTH: 213
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR437

<400> SEQUENCE: 101
cccucuguuu cauauuguau uguguuuuag uuuuguugua agucaaaauu cuuuuacuuu          60
gaccaaguuu guaguaaaau aauuaacauc uaaaauacca aauaaauaca cuauugagac        120
auauuucuug guugauuuuu cuauaaacuu ggucaaaguu agagaaguuu gacuuaggac        180
aaaacuaaac accuuaugau auggaacaga ggg                                      213

<210> SEQ ID NO 102
<211> LENGTH: 155
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR438

<400> SEQUENCE: 102
aacguguuuu gggcaaacuu guuucccac gcguuauagu gaaaacuuuu ggaauauguu          60
uguuauggga guauauauua uugauauugg aucuggugga caugguuuca aaaguuuuca        120
cuuuaacgcg ugggauauca ucuacuuccu ccguu                                    155

<210> SEQ ID NO 103

<211> LENGTH: 91
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR390

<400> SEQUENCE: 103
gguauggaac aauccuugaa gcucaggagg gauagcgccu cgaaaucaaa cuaggcgcua      60
ucuauccuga gcuccauggu uuguucuuac c                                    91

<210> SEQ ID NO 104
<211> LENGTH: 93
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR439a

<400> SEQUENCE: 104 uacccgucg aacugacgca guucgacaug uaccugucga acugugguug uucgauaggu       60 aucccgucg aaccgcgguu guucgacagg gug                                   93

<210> SEQ ID NO 105
<211> LENGTH: 60
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR439b

<400> SEQUENCE: 105
uuccugucga auuguggguug uucgauaggu acccgucg aaccgcgguu guucgacagg      60

<210> SEQ ID NO 106
<211> LENGTH: 93
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR439c

<400> SEQUENCE: 106 uacccgucg aacugacgca guucgacaug uaccugucga acugugguug uucgauaggu       60 aucccgucg aaccgcgguu guucgacagg gug                                   93

<210> SEQ ID NO 107
<211> LENGTH: 98
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR439d

<400> SEQUENCE: 107
ccaccuaccc ugucgaacuc acguaguucg acauguaccu gucgaacugu gguuguucga      60
uagguauccc ugucgaaccg cgguuguucg auagggug                             98

<210> SEQ ID NO 108
<211> LENGTH: 98

<212> TYPE: RNA
<213> ORGANISM: Artificial Sequence
<220> FEATURE:
<223> OTHER INFORMATION: Indica rice (Oryza sativa spp. indica) microRNA
    precursor (pre-miRNA) fold-back hairpin structure
    for OsmiR439e

<400> SEQUENCE: 108
ccaccuaccc ugucgaacug acgcaguucg acauguaccu gucgaacugu gguuguucga    60
uagguauccc ugucgaaccg cgguuguucg acagggug                           98

<210> SEQ ID NO 109
<211> LENGTH: 96
<212> TYPE: RNA
<213> ORGANISM: Artificial Sequence
<220> FEATURE:
<223> OTHER INFORMATION: Indica rice (Oryza sativa spp. indica) microRNA
    precursor (pre-miRNA) fold-back hairpin structure
    for OsmiR439f

<400> SEQUENCE: 109
accuacccug ucgaacugac gcaguucgac auguaccugu cgaacugugg uuguucgaua    60
gguaucccug ucgaaccgcg guuguucgac agggug                             96

<210> SEQ ID NO 110
<211> LENGTH: 88
<212> TYPE: RNA
<213> ORGANISM: Artificial Sequence
<220> FEATURE:
<223> OTHER INFORMATION: Indica rice (Oryza sativa spp. indica) microRNA
    precursor (pre-miRNA) fold-back hairpin structure
    for OsmiR439g

<400> SEQUENCE: 110
uccugucgaa cugacgcagu ucgacaugua ccugucgaac ugugguuguu cgauagguau    60
cccugucgaa ccgcgguugu ucgacagg                                      88

<210> SEQ ID NO 111
<211> LENGTH: 99
<212> TYPE: RNA
<213> ORGANISM: Artificial Sequence
<220> FEATURE:
<223> OTHER INFORMATION: Indica rice (Oryza sativa spp. indica) microRNA
    precursor (pre-miRNA) fold-back hairpin structure
    for OsmiR439h

<400> SEQUENCE: 111
accaccuacc cugucgaacu cacgcaguuc gacauguacc ugucgaacug ugguuguucg    60
auagguaucc cugucgaacc gcgguuguuc gacagggug                          99

<210> SEQ ID NO 112
<211> LENGTH: 103
<212> TYPE: RNA
<213> ORGANISM: Artificial Sequence
<220> FEATURE:
<223> OTHER INFORMATION: Indica rice (Oryza sativa spp. indica) microRNA
    precursor (pre-miRNA) fold-back hairpin structure
    for OsmiR439i

<400> SEQUENCE: 112
caccuacccu gucgaacuga cgcaguucga cauguaccug ucgaacugug guuguucgau    60
agguaucccu gucgaaccgc gguuguucga cagggugcua aac                     103

<210> SEQ ID NO 113

```
<211> LENGTH: 109
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR439j

<400> SEQUENCE: 113
acaggguacc cuaucgaaca acugcgguuc gacagguacc uauuggacug ccacacuuug    60
acaggcuagu gguccuguc gaaccgcggu guucgauag guacccugu                109

<210> SEQ ID NO 114
<211> LENGTH: 119
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR440

<400> SEQUENCE: 114
auugcuauug uuggugcugg gcucguccug aucacuagga gacucugauc aagcuaggcu    60
aaacuuaugu auuagugucu ccugaugauc gggacaaggc uaacaccgau gagagcgau   119

<210> SEQ ID NO 115
<211> LENGTH: 112
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR396d

<400> SEQUENCE: 115
aaagaugugc gggcaugcuu uccacaggcu uucuugaacu gugaacucgu gggggguguau    60 gugcucaugg uugaugguuc aagaaagccc auggaaacca ugccgcgucu uu          112

<210> SEQ ID NO 116
<211> LENGTH: 98
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR396e

<400> SEQUENCE: 116
gcgggcaugc uuccacagg cuuucuugaa cugugaacuc gugggggugu augugcucau    60
gguugauggu ucaagaaagc ccauggaaac caugccgc                           98

<210> SEQ ID NO 117
<211> LENGTH: 153
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR441a

<400> SEQUENCE: 117
aaaauauauu aauugguacu uucucuauuu aacaauguaa gucauuuuag cauuucacac    60
auucauauug aucuagauuc auuaccauca auauaaaugu gggaaaugcu aaaaugacuu   120
acauugugaa acggagggag uaguaauuca aaa                                153
```

<210> SEQ ID NO 118
<211> LENGTH: 152
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR441b

<400> SEQUENCE: 118
uuaucaccac ugacauacuu ccuccguuuc acaauguaag ucauuuuagu aauuuucaua        60
uucauauuga uguuaaugaa ucuagacuca uguaccauca auauaaaugu gggaaauggu       120
agaaugacuu acauuaugaa acauagggag ca                                     152

<210> SEQ ID NO 119
<211> LENGTH: 154
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR441c

<400> SEQUENCE: 119
uacuuccucu guuucauaau guaagucauu uuagcauuuu ucauauuuau auugauggua        60
augaaucuag auagauauau augucuagau ucauuaccau caauauaaau gugggaaaug       120
cuagaauaac uuacauugug aaacggagga agua                                   154

<210> SEQ ID NO 120
<211> LENGTH: 233
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR442

<400> SEQUENCE: 120
cacauauaug gaguauuaaa uauaaaugaa aaaauaacu aauuauacag augacguga         60 aauugcgaga cgaaucuuuu aagccuaauu gcccaugau cugacaaugu ggugcuacag       120
uaaacauuug cuaaugacgg auuaauuagg cuuaauaaau ucgucucgca guuuacagac       180
ggauucugua auuuguuuug uuauuagucu acguuaaaua cuucaaaugu gug              233

<210> SEQ ID NO 121
<211> LENGTH: 148
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR443

<400> SEQUENCE: 121
cgucccauaa aaacaaaccc aaaacuagau gugauauauc acaauacaau aaaucuggau        60
aggagucuau ccagauacuu cuaucuagau uuauuguacu gggauaguc acauauauuc       120 aguuuuauau uuguuuuuuu uuuggacg                                          148

<210> SEQ ID NO 122
<211> LENGTH: 251
<212> TYPE: RNA

<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR445a

<400> SEQUENCE: 122
ucacaucgaa uguuugacgc uaauuuggag uauuaaacau agacuaauaa aaaaacuaau      60
uucauaaaug aaagcuaauc ugcgagacga auuuuuaag ccuaauuaau ccauaauuau      120
gaaaaguuua cuaaucaugg uguaauuaga cucaaaagau cgucucgcg aauuagucca      180 agguuauaga auagguuuua uaauuagugu auguuuaaua cucuaaauua guguauaaac     240
auccgaugug a                                                          251

<210> SEQ ID NO 123
<211> LENGTH: 264
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR445b

<400> SEQUENCE: 123
guccguguca caucgaaugu uugacgcuaa uuuagaguau uaaacauaga cuaauaaaaa      60
acuaauuuca uaaaugaaag cuaaucugcg agacgaacuu uuuaagccua auuaauccau     120
aauuaugaaa aguuuacuaa ucauggugua auuagacuca aaagauucgu cucgcgaauu     180
aguccaaggu uauagaauag guuuuauaau uaauguaugu uuaauacucu aaauuagugu     240
auaaacaucc gaugugacag ggac                                            264

<210> SEQ ID NO 124
<211> LENGTH: 260
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR445c

<400> SEQUENCE: 124
ccgugucaca ucgaauguuu gacgcuaauu uggaguauua aacauagacu aauaaaaaaa      60
cuaauuucau aaaugaaagc uaaucugcga gacgaauuuu uuaagccuaa uuaauccaua     120
auuaugaaaa guuuacuaau caugguguaa uuaggcuuaa aagauucguc ucugaauua     180 guccaagguu auagaauagg uuuuauaauu aguauauauu uaauacucua aauuagugua     240
uaaacauccg augugacaua                                                 260

<210> SEQ ID NO 125
<211> LENGTH: 312
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR445d

<400> SEQUENCE: 125
uggccaaaau uuagucccug ucaucagaa uguuaugaca cuaauuaaaa guauuaaaca       60
uagacuaaug acaaacccca uuccauaacc cuggauuaau ucgcgagaug aaucuauuga    120
gucuaauuaa ucaugauua gccuauguga ugcuacacua aacauguguu aauuaugau      180 uaauuaggcu uaaaaauuuu gucucacgaa uuagcucuca uuuaugcaau uauuaguuuu    240
guaaguaguu uauguuuaau aucuaaauua guguauaaac auccgaugug auagggacua    300
aaguuggauc ca    312

```
<210> SEQ ID NO 126
<211> LENGTH: 265
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR445e

<400> SEQUENCE: 126
```
guccguguca caucgaaugu uugacgcuaa uuuggaguau uaaacauaga cuaauaaaaa    60
aacuaauuuc auaaaugaaa gcuaaucugc gagacgaauu uuuuaagccu aauuaaucca    120
uaauuaugaa aaguuuacua aucauggugu aauuagcacuc aaaagauucg ucucgcgaau    180
uaguccaagg uuauagaaua gguuuuauaa uuaguguaug uuuaauacuc uaaauuagug    240
uauaaacauc cgaugugaca gggac    265

```
<210> SEQ ID NO 127
<211> LENGTH: 305
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR445f

<400> SEQUENCE: 127
``` agaugggcu aaaacuuuuu aguccguguc acaucgaaug uuugacgcua auuggagua    60 uuaaacauag acuaauaaaa aaacuaauuu cauaaaugaa agcuaaucug cgggacgaau    120
uuuuuaagcc uaauuaaucc auaauuauga aaaguuuacu aaucaugguc uaauuagacu    180
caaaagauuc gucucgcgaa uuaguccaag guuauagaau agguuuuaua auuaguguau    240
guuuaauacu cuaaauuagu guauaaacau ccgaugugac agggacuuaa aauaagcccc    300
uguuu    305

```
<210> SEQ ID NO 128
<211> LENGTH: 275
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR445g

<400> SEQUENCE: 128
```
uuuuaguccg ugucacaucg aauguuugac gcuaauuugg aguauuaaac auagacuaau    60 aaaaaacua auuucauaaa ugaaagcuaa ucugcgagac gaauuuuuua agccuaauua    120
auccauaauu augaaaaguu uacuaaucau ggucuaauua aacucaaaag auucgucuug    180
cgaauuaguc caagguuaua gaauauguuu uauaauuagu guauguuuaa uaucuaaau    240 uaguguauaa acauccgaug ugacagggac uuaaa    275

```
<210> SEQ ID NO 129
<211> LENGTH: 277
<212> TYPE: RNA
```

<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR445h

<400> SEQUENCE: 129

```
uuuuuaguuc gugucacauu gaauguuuga cacuaauuug gaguauuaaa cauagacuaa    60
uaaaaaaacu aauuucauaa augaaagcua aucugcgaga cgaauuuuuu aagccuaauu   120
aauccauaau uaugaaaagu uacuaauca ugguguaauu agacucaaaa gauucgcuc    180 gcgaauuagu ccaagguuau agaauagguu uauaauuag uguauguuua auacucuaaa   240
uuaguguaua aacauccgau gugacaggga cuuaaaa                           277
```

<210> SEQ ID NO 130
<211> LENGTH: 244
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR445i

<400> SEQUENCE: 130

```
acuuuuagu ccgugucaca ucgaauguuu gacgcuaauu uagaguauua aauauagacu    60
aauaaaaaaa cuaauuucau aaaugaaagc uaaucuguga gaugaauuuu uaagccuaau  120
uaauccauaa uuaaaagauu cgucucgcga auuaguccaa gguuauagaa uagguuuuau  180
aauuagugua uguuuaauac uuuaaauuag uguauaaaca uccgauguga cagggacuuu  240
aagu                                                               244
```

<210> SEQ ID NO 131
<211> LENGTH: 175
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back hairpin structure
      for OsmiR446

<400> SEQUENCE: 131

```
aaauauguac uuccuuuguu ucacagugua agucauuaua aaauucccca cauuuauauu    60
gauguuaaug aaucuauaua gauauauaug ucuagauuua uuaacaucaa uaugaauaug  120
ggaaauggua gaauaacuua cauugugaaa cggagggagu auauagaacu ugaac        175
```

<210> SEQ ID NO 132
<211> LENGTH: 21
<212> TYPE: DNA
<213> ORGANISM: Artificial Sequence
<220> FEATURE:
<223> OTHER INFORMATION: Arabidopsis thaliana and Populus trichocarpa
      microRNA (miRNA) miR390

<400> SEQUENCE: 132

```
aagctcagga gggatagcgc c                                             21
```

<210> SEQ ID NO 133
<211> LENGTH: 97
<212> TYPE: RNA
<213> ORGANISM: Artificial Sequence
<220> FEATURE:
<223> OTHER INFORMATION: Arabidopsis thaliana microRNA precursor
      (pre-miRNA) fold-back structure for miR390

```
<400> SEQUENCE: 133
agauugagua guagagaaau agcuauaaag cucaggaggg auagcgccau ggcucaccug      60
gcgcuaucca uccugaguuc cauagcuucu ucuugcu                              97

<210> SEQ ID NO 134
<211> LENGTH: 132
<212> TYPE: RNA
<213> ORGANISM: Artificial Sequence
<220> FEATURE:
<223> OTHER INFORMATION: Arabidopsis thaliana microRNA precursor
      (pre-miRNA) fold-back structure for miR390

<400> SEQUENCE: 134
caaaaaaaca aaguagagaa gaaucuguaa agcucaggag ggauagcgcc augaugauca     60
cauucguuau cuauuuuuug gcgcuaucca uccugaguuu cauggcucu ucuuacuaca     120 augaaaaagg cc                                                        132

<210> SEQ ID NO 135
<211> LENGTH: 21
<212> TYPE: DNA
<213> ORGANISM: Artificial Sequence
<220> FEATURE:
<223> OTHER INFORMATION: Arabidopsis thaliana and Populus trichocarpa
      microRNA (miRNA) miR390

<400> SEQUENCE: 135
aaactcagga tggatagcgc c                                               21

<210> SEQ ID NO 136
<211> LENGTH: 140
<212> TYPE: RNA
<213> ORGANISM: Artificial Sequence
<220> FEATURE:
<223> OTHER INFORMATION: Arabidopsis thaliana microRNA precursor
      (pre-miRNA) fold-back structure for miR390

<400> SEQUENCE: 136
cggccuuuuu cauuguagua agaagagcca augaaacuca ggauggauag cgccaaaaaa     60
uagauaacga augugaucau cauggcgcua ucccuccuga gcuuuacaga uucuucucua    120
cuuuguuuuu uugggguugug                                               140

<210> SEQ ID NO 137
<211> LENGTH: 156
<212> TYPE: RNA
<213> ORGANISM: Artificial Sequence
<220> FEATURE:
<223> OTHER INFORMATION: Populus trichocarpa microRNA precursor
      (pre-miRNA) fold-back structure for miR390

<400> SEQUENCE: 137
ugauaugugc auaaguaugg gaggaucugu uaagcucagg agggauagcg ccaugagcug     60
augauaaguu gauguuugau ggguuaaucu caacauaaac aaucuaguca uuaguggcgc    120
uaucuauccu gaguucuaua gguucuccuu gcuauu                              156

<210> SEQ ID NO 138
<211> LENGTH: 138
<212> TYPE: RNA
<213> ORGANISM: Artificial Sequence
<220> FEATURE:
<223> OTHER INFORMATION: Populus trichocarpa microRNA precursor
      (pre-miRNA) fold-back structure for miR390
```

-continued

```
<400> SEQUENCE: 138
cuugauauau agaaguaugg aagaaucugu uaagcucagg agggauagcg cccuaaggau      60
aaccaugggc ucuuuuauu ugguuuuga cuaucagugg cgcuaccau ccugaguuuu        120 acugguucuu cuugcuac                                                    138

<210> SEQ ID NO 139
<211> LENGTH: 129
<212> TYPE: RNA
<213> ORGANISM: Artificial Sequence
<220> FEATURE:
<223> OTHER INFORMATION: Populus trichocarpa microRNA precursor
      (pre-miRNA) fold-back structure for miR390

<400> SEQUENCE: 139
gggagaaucu guuaagcuca ggagggauag cgccaugagc augacaaagu cuauguuuga     60
guuaaucuca acaaaaucaa uccagucauc aguggcgcua ucauccuga guucuauggg     120 uucuccuua                                                             129

<210> SEQ ID NO 140
<211> LENGTH: 134
<212> TYPE: RNA
<213> ORGANISM: Artificial Sequence
<220> FEATURE:
<223> OTHER INFORMATION: Populus trichocarpa microRNA precursor
      (pre-miRNA) fold-back structure for miR390

<400> SEQUENCE: 140
auagaaaagu auggaagaau cuguuaagcu caggagggau agcgcccuaa ggauaaucau     60
gggcucuuuu uaugugguuu uugauucuca guggcgcuau ccauccugag uuucauugcu    120
ucuucuugcu acca                                                       134

<210> SEQ ID NO 141
<211> LENGTH: 118
<212> TYPE: RNA
<213> ORGANISM: Artificial Sequence
<220> FEATURE:
<223> OTHER INFORMATION: Populus trichocarpa microRNA precursor
      (pre-miRNA) fold-back structure for miR390

<400> SEQUENCE: 141
aagaagaacc aguaaaacuc aggauggaua gcgccacuga uagucaaaaa ccaaauaaaa     60
agagcccaug guuauccuua gggcgcuauc ccuccugagc uuaacagauu cuuccaua      118

<210> SEQ ID NO 142
<211> LENGTH: 133
<212> TYPE: RNA
<213> ORGANISM: Artificial Sequence
<220> FEATURE:
<223> OTHER INFORMATION: Populus trichocarpa microRNA precursor
      (pre-miRNA) fold-back structure for miR390

<400> SEQUENCE: 142
ggagcuggua gcaagaagaa gcaaugaaac ucaggaugga uagcgccacu gagaaucaaa     60
aaccacauaa aaagagccca ugauuauccu uagggcgcua uccccccuga gcuuaacaga    120
uucuuccaua cuu                                                        133

<210> SEQ ID NO 143
<211> LENGTH: 198
<212> TYPE: RNA
<213> ORGANISM: Artificial Sequence
```

```
<220> FEATURE:
<223> OTHER INFORMATION: Maize microRNA precursor (pre-miRNA) fold-back
      structure for miR437

<400> SEQUENCE: 143
uauuuuagcc uugcccuaau uuagacuucu cuacucugac caugumuauu aaaaaugcag    60
aaacaucuac aauauuaaac cauuagauac accugaaau auuugauag uauguuuauu    120 ugauauuuua gaugcuaaca uauuuuucua uaaacauuuc aaagcuagag aaguugacu    180 ugggacaaag uuaaaaug                                                 198

<210> SEQ ID NO 144
<211> LENGTH: 239
<212> TYPE: RNA
<213> ORGANISM: Artificial Sequence
<220> FEATURE:
<223> OTHER INFORMATION: sugarcane microRNA precursor (pre-miRNA)
      fold-back structure for miR390
<220> FEATURE:
<221> NAME/KEY: modified_base
<222> LOCATION: (198)...(198)
<223> OTHER INFORMATION: n = g, a, c or u

<400> SEQUENCE: 144
uacucucugu uccaaguuau aguuuacuac uaaacuucag cuuuguccca agucaaaccu    60
cucuaacuuu gaucaaguuu auagaaaaau gcaccaaaau cuaaaauauc aaacuaguuc   120
cauuaaauuc uccaugaauu guagaugaua auauauuuuu ucuaaaaacu ugaucaaagu   180
uagagaaguu ugacuuanga caaagcuaaa gugaacaaua guuugaaacg gcgggagua   239

<210> SEQ ID NO 145
<211> LENGTH: 207
<212> TYPE: RNA
<213> ORGANISM: Artificial Sequence
<220> FEATURE:
<223> OTHER INFORMATION: Sorghum microRNA precursor (pre-miRNA)
      fold-back structure for miR390

<400> SEQUENCE: 145
uuccaaaaug uugguuguuu uaguuuuugu cauaaguaaa uucucuccaa cuuugaccaa    60
guuuauagaa aaauacaccaa cauggcaaca ucuacaaaau gaaaugaauu ucgugguauu   120
gcugauguua guauauuuuu cuacaaacuu gguuaaaguu agagaaguuu gacuuaugau   180
aaaaccaaaa cgaccuacau uuuggag                                      207

<210> SEQ ID NO 146
<211> LENGTH: 132
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back structure for
      P18-F1

<400> SEQUENCE: 146
uguuaaacgg cacgguuuuc uuggaucucu cucucccuug aaggcuaucu cauggagguu    60
ugauguacac cauuguugcc uaagaaacug agaaagccuu cggggggagga gagaagccaa   120 gcaagccaca gu                                                       132

<210> SEQ ID NO 147
<211> LENGTH: 181
<212> TYPE: RNA
<213> ORGANISM: Artificial Sequence
```

```
<220> FEATURE:
<223> OTHER INFORMATION: Indica rice (Oryza sativa spp. indica) microRNA
      precursor (pre-miRNA) fold-back structure for
      P20-A11

<400> SEQUENCE: 147
agauuuacuc cgguccaaca aaaaguaacu cgagguaccg auaccucacg guaccaaauu      60
guuuccgauc guuggaucua gcuggguggg uugggcaucg uuagauccaa cgaucggaaa     120
ugauuuugua ccgcgaggua ccgauacccuc gagauacuuu uuguuggacc gaagaaaaac    180
u                                                                    181

<210> SEQ ID NO 148
<211> LENGTH: 330
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back structure for
      P83-E9

<400> SEQUENCE: 148
aauagcucua uauaugacac aaaauuugac aauuucaccc guuccgaaaa cuaauuucgc      60
aaaugaaccg cggccaaaau uuauuucaaa aauguccccuu uuguuuagcg ccaaaucaua   120
uggcguugaa ccuaaacacc ucagcaccac gucaacuggc gcugauuaca gugccaccgu    180
ggaugggagg cugagugucu aaguucagug ucauacgaua uggcgcugaa caaaagaguc    240
auuuuuaaaa uaaguuuuag ccgcgguuca uuugcgaaac uaguuuucgg aaagggucaa    300
auugucaaau uaagugcuau auaugaaguu                                     330

<210> SEQ ID NO 149
<211> LENGTH: 204
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back structure for
      P92-A7

<400> SEQUENCE: 149
gaugcuucuu ucauccuaaa auauaagcag uuuuagaccc ugacauaguu uccgauauac     60
uacuuugauc aauacaauau acaauauaua uauauauaua uauaguaaua uguuuuaaau    120
aaaaaguugu auauugucaa aguuaaaaau guuugacuug ucacuguguu aaaaauguuu    180
auauuuuggg acggaggaag uauc                                           204

<210> SEQ ID NO 150
<211> LENGTH: 199
<212> TYPE: RNA
<213> ORGANISM: Artificial Sequence
<220> FEATURE:
<223> OTHER INFORMATION: Indica rice (Oryza sativa spp. indica) microRNA
      precursor (pre-miRNA) fold-back structure for
      P101-H12

<400> SEQUENCE: 150
cauguggcuc gcaugcuuaa auaacuaacg gcauaauuag aucacuugau gacgacguau     60
aucgguguuc gcuauauaua cuacuacug guaaguauau cuuuaauaua cuuaccagua    120
gauaguauau auagugaaca ccgauaugcg ucaucaucaa gugauuuaau uaugccguua    180
guuaagcaug cgagccaca                                                 199
```